(12) United States Patent
Macip

(10) Patent No.: US 11,175,290 B2
(45) Date of Patent: Nov. 16, 2021

(54) SENESCENT CELL BIOMARKERS

(71) Applicant: UNIVERSITY OF LEICESTER, Leicester (GB)

(72) Inventor: Salvador Macip, Leicestershire (GB)

(73) Assignee: UNIVERSITY OF LEICESTER, Leicester (GB)

( * ) Notice: Subject to any disclaimer, the term of this patent is extended or adjusted under 35 U.S.C. 154(b) by 0 days.

(21) Appl. No.: 16/665,163

(22) Filed: Oct. 28, 2019

(65) Prior Publication Data

US 2020/0182871 A1    Jun. 11, 2020

Related U.S. Application Data

(62) Division of application No. 15/313,693, filed as application No. PCT/GB2015/051480 on May 20, 2015, now Pat. No. 10,458,986.

(30) Foreign Application Priority Data

May 29, 2014   (GB) ..................... 1409519

(51) Int. Cl.
| | | |
|---|---|---|
| G01N 33/569 | (2006.01) | |
| C12Q 1/42 | (2006.01) | |
| G01N 33/68 | (2006.01) | |
| A61K 51/02 | (2006.01) | |
| C12Q 1/44 | (2006.01) | |

(52) U.S. Cl.
CPC ....... *G01N 33/56966* (2013.01); *A61K 51/02* (2013.01); *C12Q 1/42* (2013.01); *C12Q 1/44* (2013.01); *G01N 33/6842* (2013.01); *G01N 2333/705* (2013.01); *G01N 2333/916* (2013.01); *G01N 2333/918* (2013.01)

(58) Field of Classification Search
CPC ....... G01N 2333/705; G01N 2333/916; G01N 2333/918; G01N 33/56966; G01N 33/6842
See application file for complete search history.

(56) References Cited

U.S. PATENT DOCUMENTS

2005/0287140 A1   12/2005 Smothers et al.
2006/0002931 A1   1/2006 Fanslow et al.

OTHER PUBLICATIONS

Althubiti et al., Characterization of novel markers of senescence and their prognostic potential in cancer, *Cell Death Dis.*, 5:e1528 (2014).
Baker et al., Clearance of p16Ink4a-positive senescent cells delays ageing-associated disorders, *Nature*, 479(7372):232-6 (2011).
Campisi et al., Cellular senescence: when bad things happen to good cells, *Nat. Rev. Mol. Cell Biol.*, 8(9):729-40 (2007).
Castro et al., PPP1CA contributes to the senescence program induced by oncogenic Ras, *Carcinogenesis*, 29(3):491-9 (2008).
Chang et al., p21Waf1/Cip1/Sdi1-induced growth arrest is associated with depletion of mitosis-control proteins and leads to abnormal mitosis and endoreduplication in recovering cells, *Oncogene*, 19(17):2165-70 (2000).
Chen et al., Crucial role of p53-dependent cellular senescence in suppression of Pten-deficient tumorigenesis, *Nature*, 436(7051):725-30 (2005).
Collado et al., Senescence in tumours: evidence from mice and humans, *Nat. Rev. Cancer*, 10(1):51-7 (2010).
Collado et al., Tumour biology: senescence in premalignant tumours, *Nature*, 436(7051):642 (2005).
Connoy et al., Age-related changes in cell surface and senescence markers in the spleen of DBA/2 mice: a flow cytometric analysis, *Exp. Gerontol.*, 41(2):225-9 (2006).
Dankort et al., A new mouse model to explore the initiation, progression, and therapy of BRAFV600E-induced lung tumors, *Genes Dev.*, 21(4):379-84 (2007).
Dave et al., Regulated expression of PTPRJ/CD148 and an antisense long noncoding RNA in macrophages by proinflammatory stimuli, *PLoS One*, 8(6):e68306 (2013).
De Jesus et al., Assessing cell and organ senescence biomarkers, *Circ. Res.*, 111 (1):97-109 (2012).
Dimri et al., A biomarker that identifies senescent human cells in culture and in aging skin in vivo, *Proc. Natl. Acad. Sci. USA*, 92(20):9363-7 (1995).
Drummond-Barbosa, Stem cells, their niches and the systemic environment: an aging network, *Genetics*, 180(4):1787-97 (2008).
Fang et al., p21Waf1/Cip1/Sdi1 induces permanent growth arrest with markers of replicative senescence in human tumor cells lacking functional p53, *Oncogene*, 18(18):2789-97 (1999).
Hayflick et al., The serial cultivation of human diploid cell strains, *Exp. Cell Res.*, 25:585-621 (1961).
Holsinger et al., The transmembrane receptor protein tyrosine phosphatase DEP1 interacts with p120(ctn), *Oncogene*, 21(46):7067-76 (2002).
Hoshino et al., Recognition, neutralization, and clearance of target peptides in the bloodstream of living mice by molecularly imprinted polymer nanoparticles: a plastic antibody, *J. Am. Chem. Soc.*, 132(19):6644-5 (2010).
International Preliminary Report on Patentability, International Application No. PCT/GB2015/051480, dated Nov. 29, 2016.
International Search Report and Written Opinion, International Application No. PCT/GB2015/051480, dated Oct. 14, 2015.
Kellie et al., The tyrosine phosphatase DEP-1 induces cytoskeletal rearrangements, aberrant cell-substratum interactions and a reduction in cell proliferation, *J. Cell Sci.*, 117(Pt. 4):609-18 (2004).
Kondoh et al., Glycolytic enzymes can modulate cellular life span, *Cancer Res.*, 65(1):177-85 (2005).
Kosar et al., Senescence-associated heterochromatin foci are dispensable for cellular senescence, occur in a cell type- and insult-dependent manner and follow expression of p16(ink4a), *Cell Cycle*, 10(3):457-68 (2011).

(Continued)

*Primary Examiner* — Ruixiang Li
(74) *Attorney, Agent, or Firm* — Marshall, Gerstein & Borun LLP

(57) ABSTRACT

The invention relates to senescent cell biomarkers and the uses thereof. The invention also extends to methods and kits for detecting senescence, and drug conjugates and pharmaceutical compositions for killing senescent cells.

5 Claims, 11 Drawing Sheets

Figure 1A:
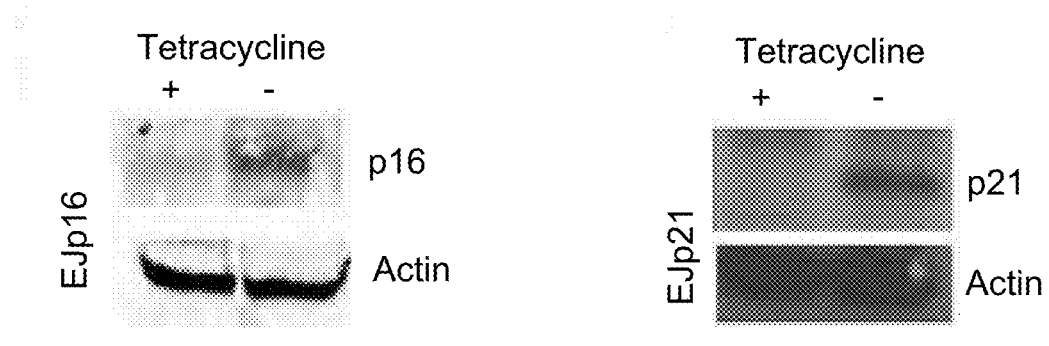

Specification includes a Sequence Listing.

(56) References Cited

OTHER PUBLICATIONS

Kuilman et al., The essence of senescence, *Genes Dev.*, 24(22):2463-79 (2010).
Lee et al., Senescence-associated beta-galactosidase is lysosomal beta-galactosidase, *Aging Cell*, 5(2):187-95 (2006).
Lowe et al., Intrinsic tumour suppression, *Nature*, 423(7015):307-15 (2004).
Macip et al., Influence of induced reactive oxygen species in p53-mediated cell fate decisions, *Mol. Cell Biol.*, 23(23):8576-85 (2003).
Macip et al., Inhibition of p21-mediated ROS accumulation can rescue p21-induced senescence, *EMBO J.*, 21(9):2180-8 (2002).
Majumder et al., A prostatic intraepithelial neoplasia-dependent p27 Kip1 checkpoint induces senescence and inhibits cell proliferation and cancer progression, *Cancer Cell*, 14(2):146-55 (2008).
Mantovani, Editorial, *Semin. Cancer Biol.*, 14:147-8 (2004).
Masgras et al., Reactive oxygen species and mitochondrial sensitivity to oxidative stress determine induction of cancer cell death by p21, *J. Biol. Chem.*, 287(13):9845-54 (2012).
Michaloglou et al., BRAFE600-associated senescence-like cell cycle arrest of human naevi, Nature, 436(7051):720-4 (2005).
Narita et al., A novel role for high-mobility group a proteins in cellular senescence and heterochromatin formation, Cell, 126(3):503-14 (2006).
Narita et al., Rb-mediated heterochromatin formation and silencing of E2F target genes during cellular senescence, Cell, 113(6):703-16 (2003).
Sarkisian et al., Dose-dependent oncogene-induced senescence in vivo and its evasion during mammary tumorigenesis, Nat. Cell Biol., 9(5):493-505 (2007).
Search Report, United Kingdom patent application No. GB1409519.4, dated Feb. 12, 2015.
Serrano et al., Oncogenic ras provokes premature cell senescence associated with accumulation of p53 and p16INK4a, Cell, 88(5):593-602 (1997).
Shevchenko et al., In-gel digestion for mass spectrometric characterization of proteins and proteomes, Nat. Protoc., 1(6):2856-60 (2006).
Tran et al., Aging-related attenuation of EGF receptor signaling is mediated in part by increased protein tyrosine phosphatase activity, Exp. Cell Res., 289(2):359-67 (2003).
Wang et al., Sequential activation of the MEK-extracellular signal-regulated kinase and MKK3/6-p38 mitogen-activated protein kinase pathways mediates oncogenic ras-induced premature senescence, Mol. Cell Biol., 22(10):3389-403 (2002).
Yang et al., The limitations and validities of senescence associated-beta-galactosidase activity as an aging marker for human foreskin fibroblast Hs68 cells, *Exp. Gerontol.*, 40(10):813-9 (2005).
Zhang et al., Smurf2 up-regulation activates telomere-dependent senescence, *Genes Dev.*, 18(24):3028-40 (2004).
Zlotnik, Chemokines in neoplastic progression, *Semin. Cancer Biol.*, 14(3):181-5 (2004).

HT1080p21-9

HDF

SEQUENCE LISTING

```
<160> NUMBER OF SEQ ID NOS: 19

<210> SEQ ID NO 1
<211> LENGTH: 1337
<212> TYPE: PRT
<213> ORGANISM: Homo sapiens

<400> SEQUENCE: 1

Met Lys Pro Ala Ala Arg Glu Ala Arg Leu Pro Pro Arg Ser Pro Gly
1               5                   10                  15

Leu Arg Trp Ala Leu Pro Leu Leu Leu Leu Leu Arg Leu Gly Gln
            20                  25                  30

Ile Leu Cys Ala Gly Gly Thr Pro Ser Pro Ile Pro Asp Pro Ser Val
        35                  40                  45

Ala Thr Val Ala Thr Gly Glu Asn Gly Ile Thr Gln Ile Ser Ser Thr
    50                  55                  60

Ala Glu Ser Phe His Lys Gln Asn Gly Thr Gly Thr Pro Gln Val Glu
65                  70                  75                  80

Thr Asn Thr Ser Glu Asp Gly Glu Ser Ser Gly Ala Asn Asp Ser Leu
                85                  90                  95

Arg Thr Pro Glu Gln Gly Ser Asn Gly Thr Asp Gly Ala Ser Gln Lys
            100                 105                 110
```

```
Thr Pro Ser Ser Thr Gly Pro Ser Pro Val Phe Asp Ile Lys Ala Val
            115                 120                 125

Ser Ile Ser Pro Thr Asn Val Ile Leu Thr Trp Lys Ser Asn Asp Thr
130                 135                 140

Ala Ala Ser Glu Tyr Lys Tyr Val Val Lys His Lys Met Glu Asn Glu
145                 150                 155                 160

Lys Thr Ile Thr Val Val His Gln Pro Trp Cys Asn Ile Thr Gly Leu
                165                 170                 175

Arg Pro Ala Thr Ser Tyr Val Phe Ser Ile Thr Pro Gly Ile Gly Asn
            180                 185                 190

Glu Thr Trp Gly Asp Pro Arg Val Ile Lys Val Ile Thr Glu Pro Ile
            195                 200                 205

Pro Val Ser Asp Leu Arg Val Ala Leu Thr Gly Val Arg Lys Ala Ala
210                 215                 220

Leu Ser Trp Ser Asn Gly Asn Gly Thr Ala Ser Cys Arg Val Leu Leu
225                 230                 235                 240

Glu Ser Ile Gly Ser His Glu Glu Leu Thr Gln Asp Ser Arg Leu Gln
                245                 250                 255

Val Asn Ile Ser Gly Leu Lys Pro Gly Val Gln Tyr Asn Ile Asn Pro
            260                 265                 270

Tyr Leu Leu Gln Ser Asn Lys Thr Lys Gly Asp Pro Leu Gly Thr Glu
            275                 280                 285

Gly Gly Leu Asp Ala Ser Asn Thr Glu Arg Ser Arg Ala Gly Ser Pro
290                 295                 300

Thr Ala Pro Val His Asp Glu Ser Leu Val Gly Pro Val Asp Pro Ser
305                 310                 315                 320

Ser Gly Gln Gln Ser Arg Asp Thr Glu Val Leu Leu Val Gly Leu Glu
                325                 330                 335

Pro Gly Thr Arg Tyr Asn Ala Thr Val Tyr Ser Gln Ala Ala Asn Gly
            340                 345                 350

Thr Glu Gly Gln Pro Gln Ala Ile Glu Phe Arg Thr Asn Ala Ile Gln
            355                 360                 365

Val Phe Asp Val Thr Ala Val Asn Ile Ser Ala Thr Ser Leu Thr Leu
370                 375                 380

Ile Trp Lys Val Ser Asp Asn Glu Ser Ser Ser Asn Tyr Thr Tyr Lys
385                 390                 395                 400

Ile His Val Ala Gly Glu Thr Asp Ser Ser Asn Leu Asn Val Ser Glu
                405                 410                 415

Pro Arg Ala Val Ile Pro Gly Leu Arg Ser Ser Thr Phe Tyr Asn Ile
            420                 425                 430

Thr Val Cys Pro Val Leu Gly Asp Ile Glu Gly Thr Pro Gly Phe Leu
            435                 440                 445

Gln Val His Thr Pro Pro Val Pro Val Ser Asp Phe Arg Val Thr Val
            450                 455                 460

Val Ser Thr Thr Glu Ile Gly Leu Ala Trp Ser Ser His Asp Ala Glu
465                 470                 475                 480

Ser Phe Gln Met His Ile Thr Gln Glu Gly Ala Gly Asn Ser Arg Val
                485                 490                 495

Glu Ile Thr Thr Asn Gln Ser Ile Ile Ile Gly Gly Leu Phe Pro Gly
            500                 505                 510

Thr Lys Tyr Cys Phe Glu Ile Val Pro Lys Gly Pro Asn Gly Thr Glu
            515                 520                 525

Gly Ala Ser Arg Thr Val Cys Asn Arg Thr Val Pro Ser Ala Val Phe
```

```
                    530                 535                 540
Asp Ile His Val Val Tyr Val Thr Thr Thr Glu Met Trp Leu Asp Trp
545                 550                 555                 560

Lys Ser Pro Asp Gly Ala Ser Glu Tyr Val Tyr His Leu Val Ile Glu
                565                 570                 575

Ser Lys His Gly Ser Asn His Thr Ser Thr Tyr Asp Lys Ala Ile Thr
                    580                 585                 590

Leu Gln Gly Leu Ile Pro Gly Thr Leu Tyr Asn Ile Thr Ile Ser Pro
                595                 600                 605

Glu Val Asp His Val Trp Gly Asp Pro Asn Ser Thr Ala Gln Tyr Thr
                    610                 615                 620

Arg Pro Ser Asn Val Ser Asn Ile Asp Val Ser Thr Asn Thr Thr Ala
625                 630                 635                 640

Ala Thr Leu Ser Trp Gln Asn Phe Asp Asp Ala Ser Pro Thr Tyr Ser
                    645                 650                 655

Tyr Cys Leu Leu Ile Glu Lys Ala Gly Asn Ser Ser Asn Ala Thr Gln
                660                 665                 670

Val Val Thr Asp Ile Gly Ile Thr Asp Ala Thr Val Thr Glu Leu Ile
                    675                 680                 685

Pro Gly Ser Ser Tyr Thr Val Glu Ile Phe Ala Gln Val Gly Asp Gly
                690                 695                 700

Ile Lys Ser Leu Glu Pro Gly Arg Lys Ser Phe Cys Thr Asp Pro Ala
705                 710                 715                 720

Ser Met Ala Ser Phe Asp Cys Glu Val Val Pro Lys Glu Pro Ala Leu
                    725                 730                 735

Val Leu Lys Trp Thr Cys Pro Pro Gly Ala Asn Ala Gly Phe Glu Leu
                740                 745                 750

Glu Val Ser Ser Gly Ala Trp Asn Asn Ala Thr His Leu Glu Ser Cys
                    755                 760                 765

Ser Ser Glu Asn Gly Thr Glu Tyr Arg Thr Glu Val Thr Tyr Leu Asn
770                 775                 780

Phe Ser Thr Ser Tyr Asn Ile Ser Ile Thr Thr Val Ser Cys Gly Lys
                    790                 795                 800
785

Met Ala Ala Pro Thr Arg Asn Thr Cys Thr Thr Gly Ile Thr Asp Pro
                805                 810                 815

Pro Pro Pro Asp Gly Ser Pro Asn Ile Thr Ser Val Ser His Asn Ser
                    820                 825                 830

Val Lys Val Lys Phe Ser Gly Phe Glu Ala Ser His Gly Pro Ile Lys
                835                 840                 845

Ala Tyr Ala Val Ile Leu Thr Thr Gly Glu Ala Gly His Pro Ser Ala
850                 855                 860

Asp Val Leu Lys Tyr Thr Tyr Glu Asp Phe Lys Lys Gly Ala Ser Asp
865                 870                 875                 880

Thr Tyr Val Thr Tyr Leu Ile Arg Thr Glu Glu Lys Gly Arg Ser Gln
                    885                 890                 895

Ser Leu Ser Glu Val Leu Lys Tyr Glu Ile Asp Val Gly Asn Glu Ser
                900                 905                 910

Thr Thr Leu Gly Tyr Tyr Asn Gly Lys Leu Glu Pro Leu Gly Ser Tyr
                    915                 920                 925

Arg Ala Cys Val Ala Gly Phe Thr Asn Ile Thr Phe His Pro Gln Asn
                930                 935                 940

Lys Gly Leu Ile Asp Gly Ala Glu Ser Tyr Val Ser Phe Ser Arg Tyr
945                 950                 955                 960
```

Ser Asp Ala Val Ser Leu Pro Gln Asp Pro Gly Val Ile Cys Gly Ala
            965                 970                 975

Val Phe Gly Cys Ile Phe Gly Ala Leu Val Ile Val Thr Val Gly Gly
            980                 985                 990

Phe Ile Phe Trp Arg Lys Lys Arg Lys Asp Ala Lys Asn Asn Glu Val
            995                 1000                1005

Ser Phe Ser Gln Ile Lys Pro Lys Lys Ser Lys Leu Ile Arg Val
        1010                1015                1020

Glu Asn Phe Glu Ala Tyr Phe Lys Lys Gln Gln Ala Asp Ser Asn
        1025                1030                1035

Cys Gly Phe Ala Glu Glu Tyr Glu Asp Leu Lys Leu Val Gly Ile
        1040                1045                1050

Ser Gln Pro Lys Tyr Ala Ala Glu Leu Ala Glu Asn Arg Gly Lys
        1055                1060                1065

Asn Arg Tyr Asn Asn Val Leu Pro Tyr Asp Ile Ser Arg Val Lys
        1070                1075                1080

Leu Ser Val Gln Thr His Ser Thr Asp Asp Tyr Ile Asn Ala Asn
        1085                1090                1095

Tyr Met Pro Gly Tyr His Ser Lys Lys Asp Phe Ile Ala Thr Gln
        1100                1105                1110

Gly Pro Leu Pro Asn Thr Leu Lys Asp Phe Trp Arg Met Val Trp
        1115                1120                1125

Glu Lys Asn Val Tyr Ala Ile Ile Met Leu Thr Lys Cys Val Glu
        1130                1135                1140

Gln Gly Arg Thr Lys Cys Glu Glu Tyr Trp Pro Ser Lys Gln Ala
        1145                1150                1155

Gln Asp Tyr Gly Asp Ile Thr Val Ala Met Thr Ser Glu Ile Val
        1160                1165                1170

Leu Pro Glu Trp Thr Ile Arg Asp Phe Thr Val Lys Asn Ile Gln
        1175                1180                1185

Thr Ser Glu Ser His Pro Leu Arg Gln Phe His Phe Thr Ser Trp
        1190                1195                1200

Pro Asp His Gly Val Pro Asp Thr Thr Asp Leu Leu Ile Asn Phe
        1205                1210                1215

Arg Tyr Leu Val Arg Asp Tyr Met Lys Gln Ser Pro Pro Glu Ser
        1220                1225                1230

Pro Ile Leu Val His Cys Ser Ala Gly Val Gly Arg Thr Gly Thr
        1235                1240                1245

Phe Ile Ala Ile Asp Arg Leu Ile Tyr Gln Ile Glu Asn Glu Asn
        1250                1255                1260

Thr Val Asp Val Tyr Gly Ile Val Tyr Asp Leu Arg Met His Arg
        1265                1270                1275

Pro Leu Met Val Gln Thr Glu Asp Gln Tyr Val Phe Leu Asn Gln
        1280                1285                1290

Cys Val Leu Asp Ile Val Arg Ser Gln Lys Asp Ser Lys Val Asp
        1295                1300                1305

Leu Ile Tyr Gln Asn Thr Thr Ala Met Thr Ile Tyr Glu Asn Leu
        1310                1315                1320

Ala Pro Val Thr Thr Phe Gly Lys Thr Asn Gly Tyr Ile Ala
        1325                1330                1335

<210> SEQ ID NO 2
<211> LENGTH: 940

-continued

<212> TYPE: PRT
<213> ORGANISM: Homo sapiens

<400> SEQUENCE: 2

```
Ala Gly Gly Thr Pro Ser Pro Ile Pro Asp Pro Ser Val Ala Thr Val
1               5                   10                  15

Ala Thr Gly Glu Asn Gly Ile Thr Gln Ile Ser Ser Thr Ala Glu Ser
            20                  25                  30

Phe His Lys Gln Asn Gly Thr Gly Thr Pro Gln Val Glu Thr Asn Thr
        35                  40                  45

Ser Glu Asp Gly Glu Ser Ser Gly Ala Asn Asp Ser Leu Arg Thr Pro
    50                  55                  60

Glu Gln Gly Ser Asn Gly Thr Asp Gly Ala Ser Gln Lys Thr Pro Ser
65                  70                  75                  80

Ser Thr Gly Pro Ser Pro Val Phe Asp Ile Lys Ala Val Ser Ile Ser
                85                  90                  95

Pro Thr Asn Val Ile Leu Thr Trp Lys Ser Asn Asp Thr Ala Ala Ser
            100                 105                 110

Glu Tyr Lys Tyr Val Val Lys His Lys Met Glu Asn Glu Lys Thr Ile
        115                 120                 125

Thr Val Val His Gln Pro Trp Cys Asn Ile Thr Gly Leu Arg Pro Ala
    130                 135                 140

Thr Ser Tyr Val Phe Ser Ile Thr Pro Gly Ile Gly Asn Glu Thr Trp
145                 150                 155                 160

Gly Asp Pro Arg Val Ile Lys Val Ile Thr Glu Pro Ile Pro Val Ser
                165                 170                 175

Asp Leu Arg Val Ala Leu Thr Gly Val Arg Lys Ala Ala Leu Ser Trp
            180                 185                 190

Ser Asn Gly Asn Gly Thr Ala Ser Cys Arg Val Leu Leu Glu Ser Ile
        195                 200                 205

Gly Ser His Glu Glu Leu Thr Gln Asp Ser Arg Leu Gln Val Asn Ile
    210                 215                 220

Ser Gly Leu Lys Pro Gly Val Gln Tyr Asn Ile Asn Pro Tyr Leu Leu
225                 230                 235                 240

Gln Ser Asn Lys Thr Lys Gly Asp Pro Leu Gly Thr Glu Gly Gly Leu
                245                 250                 255

Asp Ala Ser Asn Thr Glu Arg Ser Arg Ala Gly Ser Pro Thr Ala Pro
            260                 265                 270

Val His Asp Glu Ser Leu Val Gly Pro Val Asp Pro Ser Ser Gly Gln
        275                 280                 285

Gln Ser Arg Asp Thr Glu Val Leu Leu Val Gly Leu Glu Pro Gly Thr
    290                 295                 300

Arg Tyr Asn Ala Thr Val Tyr Ser Gln Ala Ala Asn Gly Thr Glu Gly
305                 310                 315                 320

Gln Pro Gln Ala Ile Glu Phe Arg Thr Asn Ala Ile Gln Val Phe Asp
                325                 330                 335

Val Thr Ala Val Asn Ile Ser Ala Thr Ser Leu Thr Leu Ile Trp Lys
            340                 345                 350

Val Ser Asp Asn Glu Ser Ser Asn Tyr Thr Tyr Lys Ile His Val Val
        355                 360                 365

Ala Gly Glu Thr Asp Ser Ser Asn Leu Asn Val Ser Glu Pro Arg Ala
    370                 375                 380

Val Ile Pro Gly Leu Arg Ser Ser Thr Phe Tyr Asn Ile Thr Val Cys
385                 390                 395                 400
```

-continued

```
Pro Val Leu Gly Asp Ile Glu Gly Thr Pro Gly Phe Leu Gln Val His
            405                 410                 415
Thr Pro Pro Val Pro Val Ser Asp Phe Arg Val Thr Val Val Ser Thr
        420                 425                 430
Thr Glu Ile Gly Leu Ala Trp Ser Ser His Asp Ala Glu Ser Phe Gln
        435                 440                 445
Met His Ile Thr Gln Glu Gly Ala Gly Asn Ser Arg Val Glu Ile Thr
    450                 455                 460
Thr Asn Gln Ser Ile Ile Ile Gly Gly Leu Phe Pro Gly Thr Lys Tyr
465                 470                 475                 480
Cys Phe Glu Ile Val Pro Lys Gly Pro Asn Gly Thr Glu Gly Ala Ser
                485                 490                 495
Arg Thr Val Cys Asn Arg Thr Val Pro Ser Ala Val Phe Asp Ile His
            500                 505                 510
Val Val Tyr Val Thr Thr Thr Glu Met Trp Leu Asp Trp Lys Ser Pro
        515                 520                 525
Asp Gly Ala Ser Glu Tyr Val Tyr His Leu Val Ile Glu Ser Lys His
    530                 535                 540
Gly Ser Asn His Thr Ser Thr Tyr Asp Lys Ala Ile Thr Leu Gln Gly
545                 550                 555                 560
Leu Ile Pro Gly Thr Leu Tyr Asn Ile Thr Ile Ser Pro Glu Val Asp
                565                 570                 575
His Val Trp Gly Asp Pro Asn Ser Thr Ala Gln Tyr Thr Arg Pro Ser
            580                 585                 590
Asn Val Ser Asn Ile Asp Val Ser Thr Asn Thr Thr Ala Ala Thr Leu
        595                 600                 605
Ser Trp Gln Asn Phe Asp Asp Ala Ser Pro Thr Tyr Ser Tyr Cys Leu
    610                 615                 620
Leu Ile Glu Lys Ala Gly Asn Ser Ser Asn Ala Thr Gln Val Val Thr
625                 630                 635                 640
Asp Ile Gly Ile Thr Asp Ala Thr Val Thr Glu Leu Ile Pro Gly Ser
                645                 650                 655
Ser Tyr Thr Val Glu Ile Phe Ala Gln Val Gly Asp Gly Ile Lys Ser
            660                 665                 670
Leu Glu Pro Gly Arg Lys Ser Phe Cys Thr Asp Pro Ala Ser Met Ala
        675                 680                 685
Ser Phe Asp Cys Glu Val Val Pro Lys Glu Pro Ala Leu Val Leu Lys
    690                 695                 700
Trp Thr Cys Pro Pro Gly Ala Asn Ala Gly Phe Glu Leu Glu Val Ser
705                 710                 715                 720
Ser Gly Ala Trp Asn Asn Ala Thr His Leu Glu Ser Cys Ser Ser Glu
                725                 730                 735
Asn Gly Thr Glu Tyr Arg Thr Glu Val Thr Tyr Leu Asn Phe Ser Thr
            740                 745                 750
Ser Tyr Asn Ile Ser Ile Thr Thr Val Ser Cys Gly Lys Met Ala Ala
        755                 760                 765
Pro Thr Arg Asn Thr Cys Thr Thr Gly Ile Thr Asp Pro Pro Pro Pro
    770                 775                 780
Asp Gly Ser Pro Asn Ile Thr Ser Val Ser His Asn Ser Val Lys Val
785                 790                 795                 800
Lys Phe Ser Gly Phe Glu Ala Ser His Gly Pro Ile Lys Ala Tyr Ala
                805                 810                 815
```

```
Val Ile Leu Thr Thr Gly Glu Ala Gly His Pro Ser Ala Asp Val Leu
                820                 825                 830

Lys Tyr Thr Tyr Glu Asp Phe Lys Lys Gly Ala Ser Asp Thr Tyr Val
            835                 840                 845

Thr Tyr Leu Ile Arg Thr Glu Glu Lys Gly Arg Ser Gln Ser Leu Ser
        850                 855                 860

Glu Val Leu Lys Tyr Glu Ile Asp Val Gly Asn Glu Ser Thr Thr Leu
865                 870                 875                 880

Gly Tyr Tyr Asn Gly Lys Leu Glu Pro Leu Gly Ser Tyr Arg Ala Cys
                885                 890                 895

Val Ala Gly Phe Thr Asn Ile Thr Phe His Pro Gln Asn Lys Gly Leu
            900                 905                 910

Ile Asp Gly Ala Glu Ser Tyr Val Ser Phe Ser Arg Tyr Ser Asp Ala
        915                 920                 925

Val Ser Leu Pro Gln Asp Pro Gly Val Ile Cys Gly
            930                 935                 940

<210> SEQ ID NO 3
<211> LENGTH: 243
<212> TYPE: PRT
<213> ORGANISM: Homo sapiens

<400> SEQUENCE: 3

Met Ser Ser Gly Thr Glu Leu Leu Trp Pro Gly Ala Ala Leu Leu Val
1               5                   10                  15

Leu Leu Gly Val Ala Ala Ser Leu Cys Val Arg Cys Ser Arg Pro Gly
            20                  25                  30

Ala Lys Arg Ser Glu Lys Ile Tyr Gln Gln Arg Ser Leu Arg Glu Asp
        35                  40                  45

Gln Gln Ser Phe Thr Gly Ser Arg Thr Tyr Ser Leu Val Gly Gln Ala
    50                  55                  60

Trp Pro Gly Pro Leu Ala Asp Met Ala Pro Thr Arg Lys Asp Lys Leu
65                  70                  75                  80

Leu Gln Phe Tyr Pro Ser Leu Glu Asp Pro Ala Ser Ser Arg Tyr Gln
                85                  90                  95

Asn Phe Ser Lys Gly Ser Arg His Gly Ser Glu Ala Tyr Ile Asp
            100                 105                 110

Pro Ile Ala Met Glu Tyr Tyr Asn Trp Gly Arg Phe Ser Lys Pro Pro
        115                 120                 125

Glu Asp Asp Asp Ala Asn Ser Tyr Glu Asn Val Leu Ile Cys Lys Gln
    130                 135                 140

Lys Thr Thr Glu Thr Gly Ala Gln Gln Glu Gly Ile Gly Gly Leu Cys
145                 150                 155                 160

Arg Gly Asp Leu Ser Leu Ser Leu Ala Leu Lys Thr Gly Pro Thr Ser
                165                 170                 175

Gly Leu Cys Pro Ser Ala Ser Pro Glu Glu Asp Glu Ser Glu Asp
            180                 185                 190

Tyr Gln Asn Ser Ala Ser Ile His Gln Trp Arg Glu Ser Arg Lys Val
        195                 200                 205

Met Gly Gln Leu Gln Arg Glu Ala Ser Pro Gly Pro Val Gly Ser Pro
    210                 215                 220

Asp Glu Glu Asp Gly Glu Pro Asp Tyr Val Asn Gly Glu Val Ala Ala
225                 230                 235                 240

Thr Glu Ala
```

```
<210> SEQ ID NO 4
<211> LENGTH: 6
<212> TYPE: PRT
<213> ORGANISM: Homo sapiens

<400> SEQUENCE: 4

Met Ser Ser Gly Thr Glu
1               5

<210> SEQ ID NO 5
<211> LENGTH: 358
<212> TYPE: PRT
<213> ORGANISM: Homo sapiens

<400> SEQUENCE: 5

Met Ser Ala Asp Ala Ala Gly Ala Pro Leu Pro Arg Leu Cys Cys
1               5                   10                  15

Leu Glu Lys Gly Pro Asn Gly Tyr Gly Phe His Leu His Gly Glu Lys
                20                  25                  30

Gly Lys Leu Gly Gln Tyr Ile Arg Leu Val Glu Pro Gly Ser Pro Ala
            35                  40                  45

Glu Lys Ala Gly Leu Leu Ala Gly Asp Arg Leu Val Glu Val Asn Gly
50                  55                  60

Glu Asn Val Glu Lys Glu Thr His Gln Gln Val Val Ser Arg Ile Arg
65                  70                  75                  80

Ala Ala Leu Asn Ala Val Arg Leu Leu Val Val Asp Pro Glu Thr Asp
                85                  90                  95

Glu Gln Leu Gln Lys Leu Gly Val Gln Val Arg Glu Glu Leu Leu Arg
                100                 105                 110

Ala Gln Glu Ala Pro Gly Gln Ala Glu Pro Ala Ala Ala Glu Val
            115                 120                 125

Gln Gly Ala Gly Asn Glu Asn Glu Pro Arg Glu Ala Asp Lys Ser His
            130                 135                 140

Pro Glu Gln Arg Glu Leu Arg Pro Arg Leu Cys Thr Met Lys Lys Gly
145                 150                 155                 160

Pro Ser Gly Tyr Gly Phe Asn Leu His Ser Asp Lys Ser Lys Pro Gly
                165                 170                 175

Gln Phe Ile Arg Ser Val Asp Pro Asp Ser Pro Ala Glu Ala Ser Gly
            180                 185                 190

Leu Arg Ala Gln Asp Arg Ile Val Glu Val Asn Gly Val Cys Met Glu
            195                 200                 205

Gly Lys Gln His Gly Asp Val Val Ser Ala Ile Arg Ala Gly Gly Asp
            210                 215                 220

Glu Thr Lys Leu Leu Val Val Asp Arg Glu Thr Asp Glu Phe Phe Lys
225                 230                 235                 240

Lys Cys Arg Val Ile Pro Ser Gln Glu His Leu Asn Gly Pro Leu Pro
                245                 250                 255

Val Pro Phe Thr Asn Gly Glu Ile Gln Lys Glu Asn Ser Arg Glu Ala
                260                 265                 270

Leu Ala Glu Ala Ala Leu Glu Ser Pro Arg Pro Ala Leu Val Arg Ser
            275                 280                 285

Ala Ser Ser Asp Thr Ser Glu Glu Leu Asn Ser Gln Asp Ser Pro Pro
            290                 295                 300

Lys Gln Asp Ser Thr Ala Pro Ser Ser Thr Ser Ser Ser Asp Pro Ile
305                 310                 315                 320
```

Leu Asp Phe Asn Ile Ser Leu Ala Met Ala Lys Glu Arg Ala His Gln
                325                 330                 335

Lys Arg Ser Ser Lys Arg Ala Pro Gln Met Asp Trp Ser Lys Lys Asn
            340                 345                 350

Glu Leu Phe Ser Asn Leu
        355

<210> SEQ ID NO 6
<211> LENGTH: 297
<212> TYPE: PRT
<213> ORGANISM: Homo sapiens

<400> SEQUENCE: 6

Met Arg Asp Arg Thr His Glu Leu Arg Gln Gly Asp Asp Ser Ser Asp
1               5                   10                  15

Glu Glu Asp Lys Glu Arg Val Ala Leu Val Val His Pro Gly Thr Ala
            20                  25                  30

Arg Leu Gly Ser Pro Asp Glu Glu Phe Phe His Lys Val Arg Thr Ile
        35                  40                  45

Arg Gln Thr Ile Val Lys Leu Gly Asn Lys Val Gln Glu Leu Glu Lys
    50                  55                  60

Gln Gln Val Thr Ile Leu Ala Thr Pro Leu Pro Glu Glu Ser Met Lys
65                  70                  75                  80

Gln Glu Leu Gln Asn Leu Arg Asp Glu Ile Lys Gln Leu Gly Arg Glu
                85                  90                  95

Ile Arg Leu Gln Leu Lys Ala Ile Glu Pro Gln Lys Glu Glu Ala Asp
            100                 105                 110

Glu Asn Tyr Asn Ser Val Asn Thr Arg Met Arg Lys Thr Gln His Gly
        115                 120                 125

Val Leu Ser Gln Gln Phe Val Glu Leu Ile Asn Lys Cys Asn Ser Met
    130                 135                 140

Gln Ser Glu Tyr Arg Glu Lys Asn Val Glu Arg Ile Arg Arg Gln Leu
145                 150                 155                 160

Lys Ile Thr Asn Ala Gly Met Val Ser Asp Glu Glu Leu Glu Gln Met
                165                 170                 175

Leu Asp Ser Gly Gln Ser Glu Val Phe Val Ser Asn Ile Leu Lys Asp
            180                 185                 190

Thr Gln Val Thr Arg Gln Ala Leu Asn Glu Ile Ser Ala Arg His Ser
        195                 200                 205

Glu Ile Gln Gln Leu Glu Arg Ser Ile Arg Glu Leu His Asp Ile Phe
    210                 215                 220

Thr Phe Leu Ala Thr Glu Val Glu Met Gln Gly Glu Met Ile Asn Arg
225                 230                 235                 240

Ile Glu Lys Asn Ile Leu Ser Ser Ala Asp Tyr Val Glu Arg Gly Gln
                245                 250                 255

Glu His Val Lys Thr Ala Leu Glu Asn Gln Lys Lys Ala Arg Lys Lys
            260                 265                 270

Lys Val Leu Ile Ala Ile Cys Val Ser Ile Thr Val Val Leu Leu Ala
        275                 280                 285

Val Ile Ile Gly Val Thr Val Val Gly
        290                 295

<210> SEQ ID NO 7
<211> LENGTH: 100
<212> TYPE: PRT
<213> ORGANISM: Homo sapiens

<400> SEQUENCE: 7

```
Met Ser Thr Gly Pro Thr Ala Ala Thr Gly Ser Asn Arg Arg Leu Gln
1               5                   10                  15

Gln Thr Gln Asn Gln Val Asp Glu Val Val Asp Ile Met Arg Val Asn
            20                  25                  30

Val Asp Lys Val Leu Glu Arg Asp Gln Lys Leu Ser Glu Leu Asp Asp
        35                  40                  45

Arg Ala Asp Ala Leu Gln Ala Gly Ala Ser Gln Phe Glu Thr Ser Ala
    50                  55                  60

Ala Lys Leu Lys Arg Lys Tyr Trp Trp Lys Asn Cys Lys Met Trp Ala
65                  70                  75                  80

Ile Gly Ile Thr Val Leu Val Ile Phe Ile Ile Ile Ile Val Trp
                85                  90                  95

Val Val Ser Ser
            100
```

<210> SEQ ID NO 8
<211> LENGTH: 379
<212> TYPE: PRT
<213> ORGANISM: Homo sapiens

<400> SEQUENCE: 8

```
Met Gly Tyr Ala Arg Lys Val Gly Trp Val Thr Ala Gly Leu Val Ile
1               5                   10                  15

Gly Ala Gly Ala Cys Tyr Cys Ile Tyr Arg Leu Thr Arg Gly Arg Lys
            20                  25                  30

Gln Asn Lys Glu Lys Met Ala Glu Gly Gly Ser Gly Asp Val Asp Asp
        35                  40                  45

Ala Gly Asp Cys Ser Gly Ala Arg Tyr Asn Asp Trp Ser Asp Asp Asp
    50                  55                  60

Asp Asp Ser Asn Glu Ser Lys Ser Ile Val Trp Tyr Pro Pro Trp Ala
65                  70                  75                  80

Arg Ile Gly Thr Glu Ala Gly Thr Arg Ala Arg Ala Arg Ala Arg Ala
                85                  90                  95

Arg Ala Thr Arg Ala Arg Arg Ala Val Gln Lys Arg Ala Ser Pro Asn
                100                 105                 110

Ser Asp Asp Thr Val Leu Ser Pro Gln Glu Leu Gln Lys Val Leu Cys
            115                 120                 125

Leu Val Glu Met Ser Glu Lys Pro Tyr Ile Leu Glu Ala Ala Leu Ile
        130                 135                 140

Ala Leu Gly Asn Asn Ala Ala Tyr Ala Phe Asn Arg Asp Ile Ile Arg
145                 150                 155                 160

Asp Leu Gly Gly Leu Pro Ile Val Ala Lys Ile Leu Asn Thr Arg Asp
                165                 170                 175

Pro Ile Val Lys Glu Lys Ala Leu Ile Val Leu Asn Asn Leu Ser Val
                180                 185                 190

Asn Ala Glu Asn Gln Arg Arg Leu Lys Val Tyr Met Asn Gln Val Cys
            195                 200                 205

Asp Asp Thr Ile Thr Ser Arg Leu Asn Ser Val Gln Leu Ala Gly
        210                 215                 220

Leu Arg Leu Leu Thr Asn Met Thr Val Thr Asn Glu Tyr Gln His Met
225                 230                 235                 240

Leu Ala Asn Ser Ile Ser Asp Phe Phe Arg Leu Phe Ser Ala Gly Asn
                245                 250                 255
```

```
Glu Glu Thr Lys Leu Gln Val Leu Lys Leu Leu Asn Leu Ala Glu
            260                 265                 270

Asn Pro Ala Met Thr Arg Glu Leu Arg Ala Gln Val Pro Ser Ser
            275                 280                 285

Leu Gly Ser Leu Phe Asn Lys Lys Glu Asn Lys Glu Val Ile Leu Lys
290                 295                 300

Leu Leu Val Ile Phe Glu Asn Ile Asn Asp Asn Phe Lys Trp Glu Glu
305                 310                 315                 320

Asn Glu Pro Thr Gln Asn Gln Phe Gly Glu Gly Ser Leu Phe Phe Phe
            325                 330                 335

Leu Lys Glu Phe Gln Val Cys Ala Asp Lys Val Leu Gly Ile Glu Ser
            340                 345                 350

His His Asp Phe Leu Val Lys Val Lys Val Gly Lys Phe Met Ala Lys
            355                 360                 365

Leu Ala Glu His Met Phe Pro Lys Ser Gln Glu
            370                 375

<210> SEQ ID NO 9
<211> LENGTH: 6
<212> TYPE: PRT
<213> ORGANISM: Homo sapiens

<400> SEQUENCE: 9

Met Gly Tyr Ala Arg Lys
1               5

<210> SEQ ID NO 10
<211> LENGTH: 225
<212> TYPE: PRT
<213> ORGANISM: Homo sapiens

<400> SEQUENCE: 10

Asn Arg Asp Ile Ile Arg Asp Leu Gly Gly Leu Pro Ile Val Ala Lys
1               5                   10                  15

Ile Leu Asn Thr Arg Asp Pro Ile Val Lys Glu Lys Ala Leu Ile Val
            20                  25                  30

Leu Asn Asn Leu Ser Val Asn Ala Glu Asn Gln Arg Arg Leu Lys Val
        35                  40                  45

Tyr Met Asn Gln Val Cys Asp Asp Thr Ile Thr Ser Arg Leu Asn Ser
    50                  55                  60

Ser Val Gln Leu Ala Gly Leu Arg Leu Leu Thr Asn Met Thr Val Thr
65                  70                  75                  80

Asn Glu Tyr Gln His Met Leu Ala Asn Ser Ile Ser Asp Phe Phe Arg
                85                  90                  95

Leu Phe Ser Ala Gly Asn Glu Glu Thr Lys Leu Gln Val Leu Lys Leu
            100                 105                 110

Leu Leu Asn Leu Ala Glu Asn Pro Ala Met Thr Arg Glu Leu Leu Arg
        115                 120                 125

Ala Gln Val Pro Ser Ser Leu Gly Ser Leu Phe Asn Lys Lys Glu Asn
    130                 135                 140

Lys Glu Val Ile Leu Lys Leu Leu Val Ile Phe Glu Asn Ile Asn Asp
145                 150                 155                 160

Asn Phe Lys Trp Glu Glu Asn Glu Pro Thr Gln Asn Gln Phe Gly Glu
                165                 170                 175

Gly Ser Leu Phe Phe Phe Leu Lys Glu Phe Gln Val Cys Ala Asp Lys
            180                 185                 190
```

```
Val Leu Gly Ile Glu Ser His His Asp Phe Leu Val Lys Val Lys Val
            195                 200                 205

Gly Lys Phe Met Ala Lys Leu Ala Glu His Met Phe Pro Lys Ser Gln
            210                 215                 220

Glu
225

<210> SEQ ID NO 11
<211> LENGTH: 399
<212> TYPE: PRT
<213> ORGANISM: Homo sapiens

<400> SEQUENCE: 11

Met Ala Gln Arg Ala Phe Pro Asn Pro Tyr Ala Asp Tyr Asn Lys Ser
1               5                   10                  15

Leu Ala Glu Gly Tyr Phe Asp Ala Ala Gly Arg Leu Thr Pro Glu Phe
                20                  25                  30

Ser Gln Arg Leu Thr Asn Lys Ile Arg Glu Leu Leu Gln Gln Met Glu
            35                  40                  45

Arg Gly Leu Lys Ser Ala Asp Pro Arg Asp Gly Thr Gly Tyr Thr Gly
    50                  55                  60

Trp Ala Gly Ile Ala Val Leu Tyr Leu His Leu Tyr Asp Val Phe Gly
65                  70                  75                  80

Asp Pro Ala Tyr Leu Gln Leu Ala His Gly Tyr Val Lys Gln Ser Leu
                85                  90                  95

Asn Cys Leu Thr Lys Arg Ser Ile Thr Phe Leu Cys Gly Asp Ala Gly
            100                 105                 110

Pro Leu Ala Val Ala Ala Val Leu Tyr His Lys Met Asn Asn Glu Lys
        115                 120                 125

Gln Ala Glu Asp Cys Ile Thr Arg Leu Ile His Leu Asn Lys Ile Asp
    130                 135                 140

Pro His Ala Pro Asn Glu Met Leu Tyr Gly Arg Ile Gly Tyr Ile Tyr
145                 150                 155                 160

Ala Leu Leu Phe Val Asn Lys Asn Phe Gly Val Glu Lys Ile Pro Gln
                165                 170                 175

Ser His Ile Gln Gln Ile Cys Glu Thr Ile Leu Thr Ser Gly Glu Asn
            180                 185                 190

Leu Ala Arg Lys Arg Asn Phe Thr Ala Lys Ser Pro Leu Met Tyr Glu
        195                 200                 205

Trp Tyr Gln Glu Tyr Tyr Val Gly Ala Ala His Gly Leu Ala Gly Ile
    210                 215                 220

Tyr Tyr Tyr Leu Met Gln Pro Ser Leu Gln Val Ser Gln Gly Lys Leu
225                 230                 235                 240

His Ser Leu Val Lys Pro Ser Val Asp Tyr Val Cys Gln Leu Lys Phe
                245                 250                 255

Pro Ser Gly Asn Tyr Pro Pro Cys Ile Gly Asp Asn Arg Asp Leu Leu
            260                 265                 270

Val His Trp Cys His Gly Ala Pro Gly Val Ile Tyr Met Leu Ile Gln
        275                 280                 285

Ala Tyr Lys Val Phe Arg Glu Glu Lys Tyr Leu Cys Asp Ala Tyr Gln
    290                 295                 300

Cys Ala Asp Val Ile Trp Gln Tyr Gly Leu Leu Lys Lys Gly Tyr Gly
305                 310                 315                 320

Leu Cys His Gly Ser Ala Gly Asn Ala Tyr Ala Phe Leu Thr Leu Tyr
```

```
                    325                 330                 335
Asn Leu Thr Gln Asp Met Lys Tyr Leu Tyr Arg Ala Cys Lys Phe Ala
                340                 345                 350
Glu Trp Cys Leu Glu Tyr Gly Glu His Gly Cys Arg Thr Pro Asp Thr
            355                 360                 365
Pro Phe Ser Leu Phe Glu Gly Met Ala Gly Thr Ile Tyr Phe Leu Ala
        370                 375                 380
Asp Leu Leu Val Pro Thr Lys Ala Arg Phe Pro Ala Phe Glu Leu
385                 390                 395
```

<210> SEQ ID NO 12
<211> LENGTH: 26
<212> TYPE: PRT
<213> ORGANISM: Homo sapiens

<400> SEQUENCE: 12

```
Asp Val Phe Gly Asp Pro Ala Tyr Leu Gln Leu Ala His Gly Tyr Val
1               5                   10                  15
Lys Gln Ser Leu Asn Cys Leu Thr Lys Arg
            20                  25
```

<210> SEQ ID NO 13
<211> LENGTH: 99
<212> TYPE: PRT
<213> ORGANISM: Homo sapiens

<400> SEQUENCE: 13

```
Glu Lys Ile Pro Gln Ser His Ile Gln Ile Cys Glu Thr Ile Leu
1               5                   10                  15
Thr Ser Gly Glu Asn Leu Ala Arg Lys Arg Asn Phe Thr Ala Lys Ser
            20                  25                  30
Pro Leu Met Tyr Glu Trp Tyr Gln Glu Tyr Tyr Val Gly Ala Ala His
        35                  40                  45
Gly Leu Ala Gly Ile Tyr Tyr Tyr Leu Met Gln Pro Ser Leu Gln Val
    50                  55                  60
Ser Gln Gly Lys Leu His Ser Leu Val Lys Pro Ser Val Asp Tyr Val
65                  70                  75                  80
Cys Gln Leu Lys Phe Pro Ser Gly Asn Tyr Pro Pro Cys Ile Gly Asp
                85                  90                  95
Asn Arg Asp
```

<210> SEQ ID NO 14
<211> LENGTH: 29
<212> TYPE: PRT
<213> ORGANISM: Homo sapiens

<400> SEQUENCE: 14

```
Asp Met Lys Tyr Leu Tyr Arg Ala Cys Lys Phe Ala Glu Trp Cys Leu
1               5                   10                  15
Glu Tyr Gly Glu His Gly Cys Arg Thr Pro Asp Thr Pro
            20                  25
```

<210> SEQ ID NO 15
<211> LENGTH: 119
<212> TYPE: PRT
<213> ORGANISM: Homo sapiens

<400> SEQUENCE: 15

Met Ser Arg Ser Val Ala Leu Ala Val Leu Ala Leu Leu Ser Leu Ser

-continued

```
              1               5                  10                 15
            Gly Leu Glu Ala Ile Gln Arg Thr Pro Lys Ile Gln Val Tyr Ser Arg
                          20                  25                 30

His Pro Ala Glu Asn Gly Lys Ser Asn Phe Leu Asn Cys Tyr Val Ser
                          35                  40                 45

Gly Phe His Pro Ser Asp Ile Glu Val Asp Leu Leu Lys Asn Gly Glu
                          50                  55                 60

Arg Ile Glu Lys Val Glu His Ser Asp Leu Ser Phe Ser Lys Asp Trp
            65                       70                  75                 80

Ser Phe Tyr Leu Leu Tyr Tyr Thr Glu Phe Thr Pro Thr Glu Lys Asp
                          85                  90                 95

Glu Tyr Ala Cys Arg Val Asn His Val Thr Leu Ser Gln Pro Lys Ile
                          100                 105                110

Val Lys Trp Asp Arg Asp Met
                          115

<210> SEQ ID NO 16
<211> LENGTH: 99
<212> TYPE: PRT
<213> ORGANISM: Homo sapiens

<400> SEQUENCE: 16

Ile Gln Arg Thr Pro Lys Ile Gln Val Tyr Ser Arg His Pro Ala Glu
            1               5                  10                 15

Asn Gly Lys Ser Asn Phe Leu Asn Cys Tyr Val Ser Gly Phe His Pro
                          20                  25                 30

Ser Asp Ile Glu Val Asp Leu Leu Lys Asn Gly Glu Arg Ile Glu Lys
                          35                  40                 45

Val Glu His Ser Asp Leu Ser Phe Ser Lys Asp Trp Ser Phe Tyr Leu
                          50                  55                 60

Leu Tyr Tyr Thr Glu Phe Thr Pro Thr Glu Lys Asp Glu Tyr Ala Cys
            65                       70                  75                 80

Arg Val Asn His Val Thr Leu Ser Gln Pro Lys Ile Val Lys Trp Asp
                          85                  90                 95

Arg Asp Met

<210> SEQ ID NO 17
<211> LENGTH: 490
<212> TYPE: PRT
<213> ORGANISM: Homo sapiens

<400> SEQUENCE: 17

Met Lys Pro Lys Leu Met Tyr Gln Glu Leu Lys Val Pro Ala Glu Glu
            1               5                  10                 15

Pro Ala Asn Glu Leu Pro Met Asn Glu Ile Glu Ala Trp Lys Ala Ala
                          20                  25                 30

Glu Lys Lys Ala Arg Trp Val Leu Leu Val Leu Ile Leu Ala Val Val
                          35                  40                 45

Gly Phe Gly Ala Leu Met Thr Gln Leu Phe Leu Trp Glu Tyr Gly Asp
                          50                  55                 60

Leu His Leu Phe Gly Pro Asn Gln Arg Pro Ala Pro Cys Tyr Asp Pro
            65                       70                  75                 80

Cys Glu Ala Val Leu Val Glu Ser Ile Pro Glu Gly Leu Asp Phe Pro
                          85                  90                 95

Asn Ala Ser Thr Gly Asn Pro Ser Thr Ser Gln Ala Trp Leu Gly Leu
                          100                 105                110
```

Leu Ala Gly Ala His Ser Ser Leu Asp Ile Ala Ser Phe Tyr Trp Thr
            115                 120                 125

Leu Thr Asn Asn Asp Thr His Thr Gln Glu Pro Ser Ala Gln Gln Gly
130                 135                 140

Glu Glu Val Leu Arg Gln Leu Gln Thr Leu Ala Pro Lys Gly Val Asn
145                 150                 155                 160

Val Arg Ile Ala Val Ser Lys Pro Ser Gly Pro Gln Pro Gln Ala Asp
                165                 170                 175

Leu Gln Ala Leu Leu Gln Ser Gly Ala Gln Val Arg Met Val Asp Met
            180                 185                 190

Gln Lys Leu Thr His Gly Val Leu His Thr Lys Phe Trp Val Val Asp
            195                 200                 205

Gln Thr His Phe Tyr Leu Gly Ser Ala Asn Met Asp Trp Arg Ser Leu
            210                 215                 220

Thr Gln Val Lys Glu Leu Gly Val Val Met Tyr Asn Cys Ser Cys Leu
225                 230                 235                 240

Ala Arg Asp Leu Thr Lys Ile Phe Glu Ala Tyr Trp Phe Leu Gly Gln
                245                 250                 255

Ala Gly Ser Ser Ile Pro Ser Thr Trp Pro Arg Phe Tyr Asp Thr Arg
            260                 265                 270

Tyr Asn Gln Glu Thr Pro Met Glu Ile Cys Leu Asn Gly Thr Pro Ala
            275                 280                 285

Leu Ala Tyr Leu Ala Ser Ala Pro Pro Leu Cys Pro Ser Gly Arg
            290                 295                 300

Thr Pro Asp Leu Lys Ala Leu Leu Asn Val Asp Asn Ala Arg Ser
305                 310                 315                 320

Phe Ile Tyr Val Ala Val Met Asn Tyr Leu Pro Thr Leu Glu Phe Ser
                325                 330                 335

His Pro His Arg Phe Trp Pro Ala Ile Asp Asp Gly Leu Arg Arg Ala
            340                 345                 350

Thr Tyr Glu Arg Gly Val Lys Val Arg Leu Leu Ile Ser Cys Trp Gly
            355                 360                 365

His Ser Glu Pro Ser Met Arg Ala Phe Leu Leu Ser Leu Ala Ala Leu
            370                 375                 380

Arg Asp Asn His Thr His Ser Asp Ile Gln Val Lys Leu Phe Val Val
385                 390                 395                 400

Pro Ala Asp Glu Ala Gln Ala Arg Ile Pro Tyr Ala Arg Val Asn His
                405                 410                 415

Asn Lys Tyr Met Val Thr Glu Arg Ala Thr Tyr Ile Gly Thr Ser Asn
            420                 425                 430

Trp Ser Gly Asn Tyr Phe Thr Glu Thr Ala Gly Thr Ser Leu Leu Val
            435                 440                 445

Thr Gln Asn Gly Arg Gly Gly Leu Arg Ser Gln Leu Glu Ala Ile Phe
450                 455                 460

Leu Arg Asp Trp Asp Ser Pro Tyr Ser His Asp Leu Asp Thr Ser Ala
465                 470                 475                 480

Asp Ser Val Gly Asn Ala Cys Arg Leu Leu
                485                 490

<210> SEQ ID NO 18
<211> LENGTH: 436
<212> TYPE: PRT
<213> ORGANISM: Homo sapiens

<400> SEQUENCE: 18

Gln Leu Phe Leu Trp Glu Tyr Gly Asp Leu His Leu Phe Gly Pro Asn
1               5                   10                  15

Gln Arg Pro Ala Pro Cys Tyr Asp Pro Cys Glu Ala Val Leu Val Glu
            20                  25                  30

Ser Ile Pro Glu Gly Leu Asp Phe Pro Asn Ala Ser Thr Gly Asn Pro
        35                  40                  45

Ser Thr Ser Gln Ala Trp Leu Gly Leu Leu Ala Gly Ala His Ser Ser
    50                  55                  60

Leu Asp Ile Ala Ser Phe Tyr Trp Thr Leu Thr Asn Asn Asp Thr His
65                  70                  75                  80

Thr Gln Glu Pro Ser Ala Gln Gln Gly Glu Glu Val Leu Arg Gln Leu
                85                  90                  95

Gln Thr Leu Ala Pro Lys Gly Val Asn Val Arg Ile Ala Val Ser Lys
            100                 105                 110

Pro Ser Gly Pro Gln Pro Gln Ala Asp Leu Gln Ala Leu Leu Gln Ser
        115                 120                 125

Gly Ala Gln Val Arg Met Val Asp Met Gln Lys Leu Thr His Gly Val
    130                 135                 140

Leu Ser His Thr Lys Phe Trp Val Val Asp Gln Thr His Phe Tyr Leu
145                 150                 155                 160

Gly Ser Ala Asn Met Asp Trp Arg Ser Leu Thr Gln Val Lys Glu Leu
                165                 170                 175

Gly Val Val Met Tyr Asn Cys Ser Cys Leu Ala Arg Asp Leu Thr Lys
            180                 185                 190

Ile Phe Glu Ala Tyr Trp Phe Leu Gly Gln Ala Gly Ser Ser Ile Pro
        195                 200                 205

Ser Thr Trp Pro Arg Phe Tyr Asp Thr Arg Tyr Asn Gln Glu Thr Pro
    210                 215                 220

Met Glu Ile Cys Leu Asn Gly Thr Pro Ala Leu Ala Tyr Leu Ala Ser
225                 230                 235                 240

Ala Pro Pro Pro Leu Cys Pro Ser Gly Arg Thr Pro Asp Leu Lys Ala
                245                 250                 255

Leu Leu Asn Val Val Asp Asn Ala Arg Ser Phe Ile Tyr Val Ala Val
            260                 265                 270

Met Asn Tyr Leu Pro Thr Leu Glu Phe Ser His Pro His Arg Phe Trp
        275                 280                 285

Pro Ala Ile Asp Asp Gly Leu Arg Arg Ala Thr Tyr Glu Arg Gly Val
    290                 295                 300

Lys Val Arg Leu Leu Ile Ser Cys Trp Gly His Ser Glu Pro Ser Met
305                 310                 315                 320

Arg Ala Phe Leu Leu Ser Leu Ala Ala Leu Arg Asp Asn His Thr His
                325                 330                 335

Ser Asp Ile Gln Val Lys Leu Phe Val Val Pro Ala Asp Glu Ala Gln
            340                 345                 350

Ala Arg Ile Pro Tyr Ala Arg Val Asn His Asn Lys Tyr Met Val Thr
        355                 360                 365

Glu Arg Ala Thr Tyr Ile Gly Thr Ser Asn Trp Ser Gly Asn Tyr Phe
    370                 375                 380

Thr Glu Thr Ala Gly Thr Ser Leu Leu Val Thr Gln Asn Gly Arg Gly
385                 390                 395                 400

Gly Leu Arg Ser Gln Leu Glu Ala Ile Phe Leu Arg Asp Trp Asp Ser
                405                 410                 415

```
Pro Tyr Ser His Asp Leu Asp Thr Ser Ala Asp Ser Val Gly Asn Ala
            420                 425                 430

Cys Arg Leu Leu
        435

<210> SEQ ID NO 19
<211> LENGTH: 327
<212> TYPE: PRT
<213> ORGANISM: Homo sapiens

<400> SEQUENCE: 19

Met Ser Phe Leu Gly Gly Phe Gly Pro Ile Cys Glu Ile Asp Ile
 1               5                  10                  15

Val Leu Asn Asp Gly Glu Thr Arg Lys Met Ala Glu Met Lys Thr Glu
            20                  25                  30

Asp Gly Lys Val Glu Lys His Tyr Leu Phe Tyr Asp Gly Glu Ser Val
            35                  40                  45

Ser Gly Lys Val Asn Leu Ala Phe Lys Gln Pro Gly Lys Arg Leu Glu
        50                  55                  60

His Gln Gly Ile Arg Ile Glu Phe Val Gly Gln Ile Glu Leu Phe Asn
 65                  70                  75                  80

Asp Lys Ser Asn Thr His Glu Phe Val Asn Leu Val Lys Glu Leu Ala
                85                  90                  95

Leu Pro Gly Glu Leu Thr Gln Ser Arg Ser Tyr Asp Phe Glu Phe Met
            100                 105                 110

Gln Val Glu Lys Pro Tyr Glu Ser Tyr Ile Gly Ala Asn Val Arg Leu
            115                 120                 125

Arg Tyr Phe Leu Lys Val Thr Ile Val Arg Arg Leu Thr Asp Leu Val
        130                 135                 140

Lys Glu Tyr Asp Leu Ile Val His Gln Leu Ala Thr Tyr Pro Asp Val
145                 150                 155                 160

Asn Asn Ser Ile Lys Met Glu Val Gly Ile Glu Asp Cys Leu His Ile
                165                 170                 175

Glu Phe Glu Tyr Asn Lys Ser Lys Tyr His Leu Lys Asp Val Ile Val
            180                 185                 190

Gly Lys Ile Tyr Phe Leu Leu Val Arg Ile Lys Ile Gln His Met Glu
            195                 200                 205

Leu Gln Leu Ile Lys Lys Glu Ile Thr Gly Ile Gly Pro Ser Thr Thr
        210                 215                 220

Thr Glu Thr Glu Thr Ile Ala Lys Tyr Glu Ile Met Asp Gly Ala Pro
225                 230                 235                 240

Val Lys Gly Glu Ser Ile Pro Ile Arg Leu Phe Leu Ala Gly Tyr Asp
                245                 250                 255

Pro Thr Pro Thr Met Arg Asp Val Asn Lys Lys Phe Ser Val Arg Tyr
            260                 265                 270

Phe Leu Asn Leu Val Leu Val Asp Glu Glu Asp Arg Arg Tyr Phe Lys
        275                 280                 285

Gln Gln Glu Ile Ile Leu Trp Arg Lys Ala Pro Glu Lys Leu Arg Lys
    290                 295                 300

Gln Arg Thr Asn Phe His Gln Arg Phe Glu Ser Pro Glu Ser Gln Ala
305                 310                 315                 320

Ser Ala Glu Gln Pro Glu Met
            325
```

SENESCENT CELL BIOMARKERS

The present invention relates to senescent cells, and in particular, to biomarkers that are assembled into, or associated with, the plasma membrane of senescent cells, and to methods of identifying senescent cells. The invention also extends to therapies, compositions and methods for targeting and killing senescent cells, and uses thereof.

Apoptosis and senescence have been proposed to be the two main processes that prevent the emergence of transformed cells. Senescence is defined as a permanent cell cycle arrest in which cells remain metabolically active and adopt characteristic phenotypic changes. Senescent cells often appear multinucleated, large and extended, and exhibit spindle and vacuolisation features. The establishment of this phenotype is believed to be either the result of telomere shortening after a number of cell divisions (replicative senescence) or a response to stress stimuli (stress-induced premature senescence, SIPS). Expression of oncogenes, such as Ras, cyclin E, E2F3 and Raf can also trigger senescence, which supports the tumour suppressing properties of senescence.

The presence of senescent cells in vivo is often observed in the pre-malignant stages of a tumour and they progressively disappear, suggesting that the senescent barrier needs to be overcome in order to progress into full malignancy. Moreover, cell senescence has long been associated with age-dependent organismal changes, since accumulation of senescent cells has been shown to contribute to the functional impairment of different organs. This has led to the hypothesis that senescence is an antagonistically pleiotropic process, with beneficial effects in the early decades of life of the organism as a tumour suppressor but that can be detrimental to fitness and survival in later stages due to its involvement in ageing.

One of the well-known features of both replicative and stress-induced senescence is the participation of the p53-p21 and/or p16-RB pathways. In vivo suppression of p53, and/or its upstream regulator ARF, is enough to prevent senescence in some models. However, other cell types rely primarily on p16 for senescence induction. The p53 target gene, p21, has often been considered critical for establishing senescence, whereas p16 could be more involved in the maintenance of the phenotype, together with an increase in intracellular Reactive Oxygen Species (ROS). Other genes upregulated in senescent cells are PPP1A, Smurf2 and PGM.

Cellular senescence is also associated with the secretion of growth factors, chemokines and cytokines, known as the senescence-associated secretary phenotype (SASP). SASPs have shown an effect on cell proliferation and angiogenesis, as well as in promoting ageing. Also, SASP can induce migration of leukocytes and tumour cells, which in turn may induce tumour metastasis. Increased expression of intracellular and/or secreted proteins has often been used as a surrogate marker of senescence, although it is not a specific measurement.

Senescent cells also display different modifications in the organisation of chromatin that can help identify them. In normal cells, DNA staining reveals completely uniform colour outlines, whereas senescent cells usually show dot-like patterns, known as senescence-associated heterochromatic foci (SAHF). This phenomenon is due to intensive remodelling in the chromatin, which results in less susceptibility for digestion by nucleases. SAHF development is not necessary for senescence to occur, and this depends primarily on cell types and senescent stimuli.

Apart from all this, the most distinctive measurable feature of senescent cells is the presence of β-galactosidase enzymatic activity. This enzyme normally displays activity at pH 4.0 within lysosomes, but in senescent cells it is also active at pH 6.0. This phenomenon is termed senescence associated-β-galactosidase (SA-β-Gal). Although the reasons for this are not completely clear, it is thought to be due to an enlargement in the structure of lysosomes in senescent cells. SA-β-Gal has not been shown to have any role in the establishment or maintenance of the senescent phenotype. Although it is currently the standard for the detection of senescent cells, high cell confluence and treatment with hydrogen peroxide can also stimulate SA-β-Gal activity, leading to many false positives. None of the currently available markers satisfactorily or conclusively identify senescent cells in vivo or in vitro, which underscores the need for better characterization tools.

Despite the considerable knowledge accumulated in the fifty years since Leonard Hayflick first described the phenomenon of senescence, the molecular pathways involved in the establishment and maintenance of the senescent phenotype still have not been fully characterized. For instance, little is known about the profile of proteins specifically expressed in the membrane of senescent cells, which could be critical for the immune clearance of senescent cells observed in certain situations.

There is therefore a need for more specific and sensitive senescent cell biomarkers.

The inventors have studied the expression profile of plasma membrane proteins in senescent cells in order to identify novel markers that could be easily recognized and propose potential effectors and modulators of the senescent pathway. Ten novel specific markers of senescence were validated, and two of these were selected in order to develop a fast and straightforward FACS-based approach to identify senescent cells. The results described herein will facilitate the study of senescent cells and provide new insights on pathways that contribute to this mechanism. In addition, identification of these ten new senescence cell biomarkers will be very useful in targeting senescent cells for treating conditions associated with cell senescence.

Thus, according to a first aspect of the invention, there is provided the use of at least one polypeptide selected from DEP-1, NTAL, EBP50, STX4, VAMP3, ARMCX-3, LANCL1, B2MG, PLD3 and VPS26A, or a variant or fragment thereof, as a senescent cell biomarker.

Advantageously, all of the senescent cell biomarkers used in accordance with the first aspect of the invention are associated with the plasma membrane of senescent cells. The biomarkers exhibit low or non-existent basal expression in non-senescent cells and/or are inducible in senescent cells. Consequently, these biomarkers are extremely specific and sensitive to detection. Some of the biomarkers according to the invention contain at least one domain or epitope, which is exposed on the extracellular surface of senescent cells (see Table 1), whereas the remaining biomarkers are expressed intracellularly and are associated with the plasma membrane of senescent cells. Biomarkers that are expressed on the surface of senescent cells enable senescent cells to be detected more quickly and easily compared to the known, and more widely used senescent cell biomarker, SA-β-Gal, which is considered an unreliable biomarker. Therefore, it will be appreciated that the senescent biomarkers disclosed herein can be readily detected using a variety of simple, conventional techniques known in the art.

TABLE 1

Subcellular location and membrane topology of biomarkers showing increased expression in senescent cells

| Senescent biomarker | Subcellular location |
|---|---|
| DEP-1 | Integral transmembrane protein of plasma membrane |
| NTAL | Integral transmembrane protein of plasma membrane |
| EBP50 | Peripheral membrane protein associated with the cytoplasmic face of the plasma membrane (intracellular) |
| STX4 | Membrane anchored protein with a large intracellular domain and no extracellular domain |
| VAMP3 | Membrane anchored protein with a large intracellular domain and no extracellular domain |
| ARMCX-3 | Integral plasma membrane protein with two transmembrane helices and two extracellular domains |
| LANCL1 | Integral plasma membrane protein with six transmembrane helices and three extracellular domains |
| B2MG | Secreted protein (extracellular) found associated with the extra-cytoplasmic face of the plasma membrane |
| PLD3 | Trans membrane protein of plasma membrane with a single extracellular domain |
| VPS26A | Peripheral membrane protein associated with the cytoplasmic face of the plasma membrane (intracellular) |

DEP-1 is an integral transmembrane membrane protein of the plasma membrane. The amino acid sequence of DEP-1 (Accession code: Q12913; also known as CD148 or PTPRJ) is referred to herein as SEQ ID No.1, as follows:

```
                                               [SEQ ID No. 1]
MKPAAREARL PPRSPGLRWA LPLLLLLLRL GQILCAGGTP

SPIPDPSVAT VATGENGITQ ISSTAESFHK QNGTGTPQVE

TNTSEDGESS GANDSLRTPE QGSNGTDGAS QKTPSSTGPS

PVFDIKAVSI SPTNVILTWK SNDTAASEYK YVVKHKMENE

KTITVVHQPW CNITGLRPAT SYVFSITPGI GNETWGDPRV

IKVITEPIPV SDLRVALTGV RKAALSWSNG NGTASCRVLL

ESIGSHEELT QDSRLQVNIS GLKPGVQYNI NPYLLQSNKT

KGDPLGTEGG LDASNTERSR AGSPTAPVHD ESLVGPVDPS

SGQQSRDTEV LLVGLEPGTR YNATVYSQAA NGTEGQPQAI

EFRTNAIQVF DVTAVNISAT SLTLIWKVSD NESSSNYTYK

IHVAGETDSS NLNVSEPRAV IPGLRSSTFY NITVCPVLGD

IEGTPGFLQV HTPPVPVSDF RVTVVSTTEI GLAWSSHDAE

SFQMHITQEG AGNSRVEITT NQSIIIGGLF PGTKYCFEIV

PKGPNGTEGA SRTVCNRTVP SAVFDIHVVY VTTTEMWLDW

KSPDGASEYV YHLVIESKHG SNHTSTYDKA ITLQGLIPGT

LYNITISPEV DHVWGDPNST AQYTRPSNVS NIDVSTNTTA

ATLSWQNFDD ASPTYSYCLL IEKAGNSSNA TQVVTDIGIT

DATVTELIPG SSYTVEIFAQ VGDGIKSLEP GRKSFCTDPA

SMASFDCEVV PKEPALVLKW TCPPGANAGF ELEVSSGAWN

NATHLESCSS ENGTEYRTEV TYLNFSTSYN ISITTVSCGK

MAAPTRNTCT TGITDPPPPD GSPNITSVSH NSVKVKFSGF

EASHGPIKAY AVILTTGEAG HPSADVLKYT YEDFKKGASD

TYVTYLIRTE EKGRSQSLSE VLKYEIDVGN ESTTLGYYNG

KLEPLGSYRA CVAGFTNITF HPQNKGLIDG AESYVSFSRY

SDAVSLPQDP GVICGAVFGC IFGALVIVTV GGFIFWRKKR

KDAKNNEVSF SQIKPKKSKL IRVENFEAYF KKQQADSNCG

FAEEYEDLKL VGISQPKYAA ELAENRGKNR YNNVLPYDIS

RVKLSVQTHS TDDYINANYM PGYHSKKDFI ATQGPLPNTL

KDFWRMVWEK NVYAIIMLTK CVEQGRTKCE EYWPSKQAQD

YGDITVAMTS EIVLPEWTIR DFTVKNIQTS ESHPLRQFHF

TSWPDHGVPD TTDLLINFRY LVRDYMKQSP PESPILVHCS

AGVGRTGTFI AIDRLIYQIE NENTVDVYGI VYDLRMHRPL

MVQTEDQYVF LNQCVLDIVR SQKDSKVDLI YQNTTAMTIY

ENLAPVTTFG KTNGYIA
```

Preferably, the extracellular domain of DEP-1 is used as a biomarker of senescent cells. The amino acid sequence of the extracellular domain of DEP-1 is referred to herein as SEQ ID No. 2, as follows:

```
                                               [SEQ ID No. 2]
AGGTPSPIPD PSVATVATGE NGITQISSTA ESFHKQNGTG

TPQVETNTSE DGESSGANDS LRTPEQGSNG TDGASQKTPS

STGPSPVFDI KAVSISPTNV ILTWKSNDTA ASEYKYVVKH

KMENEKTITV VHQPWCNITG LRPATSYVFS ITPGIGNETW

GDPRVIKVIT EPIPVSDLRV ALTGVRKAAL SWSNGNGTAS

CRVLLESIGS HEELTQDSRL QVNISGLKPG VQYNINPYLL

QSNKTKGDPL GTEGGLDASN TERSRAGSPT APVHDESLVG

PVDPSSGQQS RDTEVLLVGL EPGTRYNATV YSQAANGTEG

QPQAIEFRTN AIQVFDVTAV NISATSLTLI WKVSDNESSS

NYTYKIHVAG ETDSSNLNVS EPRAVIPGLR SSTFYNITVC

PVLGDIEGTP GFLQVHTPPV PVSDFRVTVV STTEIGLAWS

SHDAESFQMH ITQEGAGNSR VEITTNQSII IGGLFPGTKY

CFEIVPKGPN GTEGASRTVC NRTVPSAVFD IHVVYVTTTE

MWLDWKSPDG ASEYVYHLVI ESKHGSNHTS TYDKAITLQG

LIPGTLYNIT ISPEVDHVWG DPNSTAQYTR PSNVSNIDVS

TNTTAATLSW QNFDDASPTY SYCLLIEKAG NSSNATQVVT

DIGITDATVT ELIPGSSYTV EIFAQVGDGI KSLEPGRKSF

CTDPASMASF DCEVVPKEPA LVLKWTCPPG ANAGFELEVS

SGAWNNATHL ESCSSENGTE YRTEVTYLNF STSYNISITT

VSCGKMAAPT RNTCTTGITD PPPPDGSPNI TSVSHNSVKV

KFSGFEASHG PIKAYAVILT TGEAGHPSAD VLKYTYEDFK

KGASDTYVTY LIRTEEKGRS QSLSEVLKYE IDVGNESTTL

GYYNGKLEPL GSYRACVAGF TNITFHPQNK GLIDGAESYV

SFSRYSDAVS LPQDPGVICG
```

NTAL is an integral transmembrane membrane protein of the plasma membrane. The amino acid sequence of NTAL (Accession code: Q9GZY6; also known as LAT2) is referred to herein as SEQ ID No.3, as follows:

[SEQ ID No. 3]
MSSGTELLWP GAALLVLLGV AASLCVRCSR PGAKRSEKIY

QQRSLREDQQ SFTGSRTYSL VGQAWPGPLA DMAPTRKDKL

LQFYPSLEDP ASSRYQNFSK GSRHGSEEAY IDPIAMEYYN

WGRFSKPPED DDANSYENVL ICKQKTTETG AQQEGIGGLC

RGDLSLSLAL KTGPTSGLCP SASPEEDEES EDYQNSASIH

QWRESRKVMG QLQREASPGP VGSPDEEDGE PDYVNGEVAA

TEA

Preferably, the extracellular domain of NTAL is used as a biomarker of senescent cells. The amino acid sequence of the extracellular domain of NTAL is referred to herein as SEQ ID No.4, as follows:

[SEQ ID No. 4]
MSSGTE

EBP50 is an intracellular protein associated with the cytoplasmic face of the plasma membrane. The amino acid sequence of EBP50 (Accession code: O14745; also known as NHERF1) is referred to herein as SEQ ID No.5, as follows:

[SEQ ID No. 5]
MSADAAAGAP LPRLCCLEKG PNGYGFHLHG EKGKLGQYIR

LVEPGSPAEK AGLLAGDRLV EVNGENVEKE THQQVVSRIR

AALNAVRLLV VDPETDEQLQ KLGVQVREEL LRAQEAPGQA

EPPAAAEVQG AGNENEPREA DKSHPEQREL RPRLCTMKKG

PSGYGFNLHS DKSKPGQFIR SVDPDSPAEA SGLRAQDRIV

EVNGVCMEGK QHGDVVSAIR AGGDETKLLV VDRETDEFFK

KCRVIPSQEH LNGPLPVPFT NGEIQKENSR EALAEAALES

PRPALVRSAS SDTSEELNSQ DSPPKQDSTA PSSTSSSDPI

LDFNISLAMA KERAHQKRSS KRAPQMDWSK KNELFSNL

STX4 is a plasma membrane anchored protein with a large intracellular domain and no extracellular domain. The amino acid sequence of STX4 (Accession code: Q12846) is referred to herein as SEQ ID No.6, as follows:

[SEQ ID No. 6]
MRDRTHELRQ GDDSSDEEDK ERVALVVHPG TARLGSPDEE

FFHKVRTIRQ TIVKLGNKVQ ELEKQQVTIL ATPLPEESMK

QELQNLRDEI KQLGREIRLQ LKAIEPQKEE ADENYNSVNT

RMRKTQHGVL SQQFVELINK CNSMQSEYRE KNVERIRRQL

KITNAGMVSD EELEQMLDSG QSEVFVSNIL KDTQVTRQAL

NEISARHSEI QQLERSIREL HDIFTFLATE VEMQGEMINR

IEKNILSSAD YVERGQEHVK TALENQKKAR KKKVLIAICV

SITVVLLAVI IGVTVVG

VAMP3 is a plasma membrane anchored protein with a large intracellular domain and no extracellular domain. The amino acid sequence of VAMP3 (Accession code: Q15836; also known as Cellubrevin) is referred to herein as SEQ ID No.7, as follows:

[SEQ ID No. 7]
MSTGPTAATG SNRRLQQTQN QVDEVVDIMR VNVDKVLERD

QKLSELDDRA DALQAGASQF ETSAAKLKRK YWWKNCKMWA

IGITVLVIFI IIIIVWVVSS

ARMCX-3 is an integral plasma membrane protein with two transmembrane helices and two extracellular domains. The amino acid sequence of ARMCX-3 (Accession code: Q9UH62; also known as ALEX3) is referred to herein as SEQ ID No.8, as follows:

[SEQ ID No. 8]
MGYARKVGWV TAGLVIGAGA CYCIYRLTRG RKQNKEKMAE

GGSGDVDDAG DCSGARYNDW SDDDDDSNES KSIVWYPPWA

RIGTEAGTRA RARARARATR ARRAVQKRAS PNSDDTVLSP

QELQKVLCLV EMSEKPYILE AALIALGNNA AYAFNRDIIR

DLGGLPIVAK ILNTRDPIVK EKALIVLNNL SVNAENQRRL

KVYMNQVCDD TITSRLNSSV QLAGLRLLTN MTVTNEYQHM

LANSISDFFR LFSAGNEETK LQVLKLLLNL AENPAMTREL

LRAQVPSSLG SLFNKKENKE VILKLLVIFE NINDNFKWEE

NEPTQNQFGE GSLFFFLKEF QVCADKVLGI ESHHDFLVKV

KVGKFMAKLA EHMFPKSQE

Preferably, both extracellular domains of ARMCX-3 are used as a biomarker of senescent cells. The amino acid sequence of the first extracellular domain of ARMCX-3 is referred to herein as SEQ ID No. 9, as follows:

[SEQ ID No. 9]
MGYARK

The amino acid sequence of the second extracellular domain of ARMCX-3 is referred to herein as SEQ ID No. 10, as follows:

[SEQ ID No. 10]
NRDIIRDLGGLPIVAKILNTRDPIVKEKALIVLNNLSVNAENQRRLKVYM

NQVCDDTITSRLNSSVQLAGLRLLTNMTVTNEYQHMLANSISDFFRLFSA

GNEETKLQVLKLLLNLAENPAMTRELLRAQVPSSLGSLFNKKENKEVILK

LLVIFENINDNFKWEENEPTQNQFGEGSLFFFLKEFQVCADKVLGIESHH

DFLVKVKVGKFMAKLAEHMFPKSQE

LANCL1 is an integral plasma membrane protein with six transmembrane helices and three extracellular domains. The amino acid sequence of LANCL1 (Accession code: O43813) is referred to herein as SEQ ID No.11, as follows:

[SEQ ID No. 11]
MAQRAFPNPY ADYNKSLAEG YFDAAGRLTP EFSQRLTNKI

RELLQQMERG LKSADPRDGT GYTGWAGIAV LYLHLYDVFG

```
DPAYLQLAHG YVKQSLNCLT KRSITFLCGD AGPLAVAAVL

YHKMNNEKQA EDCITRLIHL NKIDPHAPNE MLYGRIGYIY

ALLFVNKNFG VEKIPQSHIQ QICETILTSG ENLARKRNFT

AKSPLMYEWY QEYYVGAAHG LAGIYYYLMQ PSLQVSQGKL

HSLVKPSVDY VCQLKFPSGN YPPCIGDNRD LLVHWCHGAP

GVIYMLIQAY KVFREEKYLC DAYQCADVIW QYGLLKKGYG

LCHGSAGNAY AFLTLYNLTQ DMKYLYRACK FAEWCLEYGE

HGCRTPDTPF SLFEGMAGTI YFLADLLVPT KARFPAFEL
```

Preferably, all three extracellular domains of LANCL1 may be used as a biomarker of senescent cells. The amino acid sequence of the first extracellular domain of LANCL1 is referred to herein as SEQ ID No.12, as follows:

```
                                        [SEQ ID No. 12]
DVFGDPAYLQLAHGYVKQSLNCLTKR
```

The amino acid sequence of the second extracellular domain of LANCL1 is referred to herein as SEQ ID No.13, as follows:

```
                                        [SEQ ID No. 13]
EKIPQSHIQQICETILTSGENLARKRNFTAKSPLMYEWYQEYYVGAAHGL

AGIYYYLMQPSLQVSQGKLHSLVKPSVDYVCQLKFPSGNYPPCIGDNRD
```

The amino acid sequence of the third extracellular domain of LANCL1 is referred to herein as SEQ ID No.14, as follows:

```
                                        [SEQ ID No. 14]
DMKYLYRACKFAEWCLEYGEHGCRTPDTP
```

B2MG is a secreted protein associated with the extra-cytoplasmic surface of the plasma membrane. The amino acid sequence of B2MG (Accession code: P61769) is referred to herein as SEQ ID No.15, as follows:

```
                                        [SEQ ID No. 15]
MSRSVALAVL ALLSLSGLEA IQRTPKIQVY SRHPAENGKS

NFLNCYVSGF HPSDIEVDLL KNGERIEKVE HSDLSFSKDW

SFYLLYYTEF TPTEKDEYAC RVNHVTLSQP KIVKWDRDM
```

The first 20 amino acids of SEQ ID No.15 are the signal peptide of B2MG. The signal peptide of B2MG is responsible for directing B2MG to the plasma membrane of the cell for translocation across the plasma membrane to become a secreted protein. The amino acid sequence of B2MG without signal peptide is referred to herein as SEQ ID No.16, as follows:

```
                                        [SEQ ID No. 16]
IQRTPKIQVY SRHPAENGKS NFLNCYVSGF HPSDIEVDLL

KNGERIEKVE HSDLSFSKDW SFYLLYYTEF TPTEKDEYAC

RVNHVTLSQP KIVKWDRDM
```

PLD3 is a transmembrane protein with a single extracellular domain. The amino acid sequence of PLD3 (Accession code: Q8IV08) is referred to herein as SEQ ID No.17, as follows:

```
                                        [SEQ ID No. 17]
MKPKLMYQEL KVPAEEPANE LPMNEIEAWK AAEKKARWVL

LVLILAVVGF GALMTQLFLW EYGDLHLFGP NQRPAPCYDP

CEAVLVESIP EGLDFPNAST GNPSTSQAWL GLLAGAHSSL

DIASFYWTLT NNDTHTQEPS AQQGEEVLRQ LQTLAPKGVN

VRIAVSKPSG PQPQADLQAL LQSGAQVRMV DMQKLTHGVL

HTKFWVVDQT HFYLGSANMD WRSLTQVKEL GVVMYNCSCL

ARDLTKIFEA YWFLGQAGSS IPSTWPRFYD TRYNQETPME

ICLNGTPALA YLASAPPPLC PSGRTPDLKA LLNVVDNARS

FIYVAVMNYL PTLEFSHPHR FWPAIDDGLR RATYERGVKV

RLLISCWGHS EPSMRAFLLS LAALRDNHTH SDIQVKLFVV

PADEAQARIP YARVNHNKYM VTERATYIGT SNWSGNYFTE

TAGTSLLVTQ NGRGGLRSQL EAIFLRDWDS PYSHDLDTSA

DSVGNACRLL
```

Preferably, the extracellular domain of PLD3 is used as a biomarker of senescent cells. The amino acid sequence of the extracellular domain of PLD3 is referred to herein as SEQ ID No. 18, as follows:

```
                                        [SEQ ID No. 18]
QLFLWEYGDLHLFGPNQRPAPCYDPCEAVLVESIPEGLDFPNASTGNPST

SQAWLGLLAGAHSSLDIASFYWTLTNNDTHTQEPSAQQGEEVLRQLQTLA

PKGVNVRIAVSKPSGPQPQADLQALLQSGAQVRMVDMQKLTHGVLsHTKF

WVVDQTHFYLGSANMDWRSLTQVKELGVVMYNCSCLARDLTKIFEAYWFL

GQAGSSIPSTWPRFYDTRYNQETPMEICLNGTPALAYLASAPPPLCPSGR

TPDLKALLNVVDNARSFIYVAVMNYLPTLEFSHPHRFWPAIDDGLRRATY

ERGVKVRLLISCWGHSEPSMRAFLLSLAALRDNHTHSDIQVKLFVVPADE

AQARIPYARVNHNKYMVTERATYIGTSNWSGNYFTETAGTSLLVTQNGRG

GLRSQLEAIFLRDWDSPYSHDLDTSADSVGNACRLL
```

VPS26A is an intracellular protein associated with the cytoplasmic face of the plasma membrane. The amino acid sequence of VPS26A (Accession code: O75436) is referred to herein as SEQ ID No.19, as follows:

```
                                        [SEQ ID No. 19]
MSFLGGFFGP ICEIDIVLND GETRKMAEMK TEDGKVEKHY

LFYDGESVSG KVNLAFKQPG KRLEHQGIRI EFVGQIELFN

DKSNTHEFVN LVKELALPGE LTQSRSYDFE FMQVEKPYES

YIGANVRLRY FLKVTIVRRL TDLVKEYDLI VHQLATYPDV

NNSIKMEVGI EDCLHIEFEY NKSKYHLKDV IVGKIYFLLV

RIKIQHMELQ LIKKEITGIG PSTTTETETI AKYEIMDGAP

VKGESIPIRL FLAGYDPTPT MRDVNKKFSV RYFLNLVLVD

EEDRRYFKQQ EIILWRKAPE KLRKQRTNFH QRFESPESQA

SAEQPEM
```

Thus, in one embodiment, preferably at least one polypeptide sequence comprising an amino acid sequence substantially as set out in any one of SEQ ID Nos. 1 to 19, or a variant or fragment thereof, is used as a senescent cell biomarker.

The inventors have found that the proteins DEP-1, NTAL, EBP50, STX4, VAMP-3, PLD3 and ARMCX-3 were specifically expressed in all senescent cells, whereas B2MG, LANCL1 and VPS26A were up-regulated only in p16-induced senescence. Therefore, preferably one or more of DEP-1, NTAL, EBP50, STX4, VAMP-3, PLD3 and ARMCX-3, or a variant or fragment thereof, is used as a senescent cell biomarker. Hence, the at least one polypeptide sequence comprises an amino acid sequence substantially as set out in any one of SEQ ID Nos. 1, 2, 3, 4, 5, 6, 7, 8, 9, 10, 17 and 18, or a variant or fragment thereof.

It is preferred however that the extracellular domains of any of the proteins described herein is used as a senescent cell biomarker. The term "fragment thereof" can therefore refer to an extracellular domain of the protein. Accordingly, preferably at least one polypeptide sequence comprising an amino acid sequence substantially as set out in any one of SEQ ID Nos. 2, 4, 9, 10, 12, 13, 14, 16 and 18, or a variant or fragment thereof, is used as an extracellular biomarker of senescent cells. Accordingly, one or more of DEP-1, NTAL, B2MG, ARMCX-3, PLD3 and LANCL1, or a variant or fragment thereof, is used as an extracellular biomarker.

Most preferably, one or more of DEP-1, NTAL, ARMCX-3 and PLD3, or a variant or fragment thereof, is used as an extracellular biomarker. Hence, preferably the at least one polypeptide sequence comprises an amino acid sequence substantially as set out in any one of SEQ ID Nos. 2, 4, 9, 10 and 18, or a variant or fragment thereof.

As described in the Examples, the inventors have demonstrated that any of the ten senescent cell biomarkers described herein can be used to specifically detect senescent cells in a biological sample.

Therefore, according to a second aspect, there is provided a method of detecting a senescent cell in a sample, the method comprises detecting the expression, in the sample, of at least one senescent cell biomarker selected from DEP-1, NTAL, EBP50, STX4, VAMP3, ARMCX-3, LANCL1, B2MG, PLD3 and VPS26A, or a variant or fragment thereof, wherein an increased level of expression of the at least one biomarker or a variant or fragment thereof relative to the level of expression detected in a reference sample is an indication of a senescent cell present in the sample.

The more biomarkers (or variants or fragments thereof) that are detected in the sample, the greater the accuracy and reliability with which senescent cells can be identified. The method may therefore comprise detecting two or more biomarkers, or variants or fragments thereof, in the sample. In another embodiment, the method may comprise detecting three or more biomarkers, or variants or fragments thereof, in the sample. Preferably, the method comprises detecting four, five, six or more of the biomarkers, or variants or fragments thereof, described herein. Most preferably, the method comprises detecting the presence of DEP-1, NTAL, EBP50, STX4, VAMP-3, PLD3 and/or ARMCX-3, or a variant or fragment thereof. The method may comprise detecting one or more of the biomarkers, according to the invention, in a sample together with other known biomarkers, such as DCR-2, Notch-3 or ICAM-1.

The term "detecting" can refer, but is not limited to, the use of any one of the following conventional assays for detecting the presence of one or more of the biomarkers, or variants or fragments thereof, in a sample: flow cytometry; immunoassays, such as enzyme-linked immunosorbent assays (ELISAs), an enzyme immunoassay (EIAs), radio-immunoassay (RIAs), Western Blots, immuo-precipitation or immunohistochemistry; chromogenic (enzyme activity) assays; fluorometric imaging plate reader (FLIPR) assay; or high performance liquid chromatography (HPLC) tandem mass spectrometry (MS/MS).

Preferably, the senescence biomarker is detected using flow cytometry. Advantageously, flow cytometry can be used to measure and distinguish between cell surface and intracellular localisation of a biomarker protein in situ. Intracellular localisation of biomarkers, according to the invention, can be detected using flow cytometry by exposing the cells in the sample to a permeabilization agent, such as saponin, which permits entry of the cytometric antibodies into the target cells.

Alternatively, the presence of one or more of the senescence biomarkers may be detected in the sample by measuring their functional activity, e.g. by enzyme assay. Alternatively, to measure the level of gene expression of the senescence biomarkers, cDNA may be generated from mRNA extracted from cells present in the sample, and primers designed to amplify test sequences using a quantitative form of Polymerase Chain Reaction.

The "sample" is preferably a bodily sample taken from a test subject. Detection for the presence of at least one senescent cell biomarker, or a variant or fragment thereof, in the sample, is therefore preferably carried out in vitro. The sample may comprise blood, plasma, serum, spinal fluid, urine, sweat, saliva, tears, breast aspirate, prostate fluid, seminal fluid, vaginal fluid, stool, cervical scraping, cytes, amniotic fluid, intraocular fluid, mucous, moisture in breath, animal tissue, cell lysates, tumour tissue, hair, skin, buccal scrapings, nails, bone marrow, cartilage, prions, bone powder, ear wax, or combinations thereof.

In another embodiment, the sample may be contained within the test subject, which may be an experimental animal (e.g. a mouse or rat) or a human, wherein the method is an in vivo based test. Alternatively, the sample may be an ex vivo sample or an in vitro sample. Therefore, the cells being tested may be in a tissue sample (for ex vivo based tests) or the cells may be grown in culture (an in vitro sample). Preferably, the biological sample is an ex vivo sample.

The method may comprise detecting the expression (or presence), in the sample, of the at least one senescent cell biomarker, wherein an increased level of expression of the at least one biomarker or a variant or fragment thereof, relative to the level of expression detected in the reference sample is an indication of a senescent cell present in the sample. Preferably, the reference sample (i.e. a control) does not comprise any senescent cells, and so does not express any of the biomarkers, or only very low or undetectable concentrations thereof.

Expression of at least one of the senescence biomarkers or a variant or fragment thereof may be detected in any compartment of the cell (e.g. in the nucleus, cytosol, the Endoplasmic Reticulum, the Golgi apparatus or the intracellular surface of the plasma membrane), or on the cell surface. Preferably, the senescence biomarker is expressed on the cell surface or physically associated with the intracellular or extracellular surface of the plasma membrane.

The inventors have developed a kit which is useful for detecting senescent cells.

According to a third aspect, there is provided a senescent cell detection kit for detecting senescent cells in a sample, the kit comprising means for detecting the presence, in a sample from a test subject, of at least one senescent cell biomarker selected from DEP-1, NTAL, EBP50, STX4, VAMP3, ARMCX-3, LANCL1, B2MG, PLD3 and VPS26A, or a variant or fragment thereof.

It will be appreciated that the inventors have determined that there are ten biomarkers which are associated with senescence, and the kits of the invention may comprise means for detecting one or more of the senescence biomarkers, or a variant or fragment thereof. The kit may therefore comprise means for detecting: DEP-1, NTAL, EBP50, STX4, VAMP3, ARMCX-3, LANCL1, B2MG, PLD3 and VPS26A, or a variant or fragment thereof, or combinations thereof.

Preferably, the kit comprises at least one control or reference sample. The kit may comprise a negative control and/or a positive control. A negative control may comprise any non-senescent cell that does not express any of the senescent biomarkers according to the invention, or only very low or undetectable concentrations thereof. A positive control may comprise any senescent cell that does express one or more of the senescent biomarkers according to the invention.

Senescent biomarkers according to the invention, which do not contain an extracellular domain may be detected using conventional techniques known in the art that are capable of detecting intracellular expression of a protein, such as Western Blots, immuno-precipitation or flow cytometry (with the aid of a permeabilisation agent, such as saponin).

The kit may comprise a means to compare the level of expression (or concentration) of the senescent biomarkers in the negative control sample to the level of expression of the equivalent biomarkers in a biological sample from an unknown subject, wherein an increased level of expression of one or more of the biomarkers relative to that detected in the negative control is an indication of senescence in the sample. Hence, by way of example, the concentration of the biomarker or a fragment or variant thereof in a sample with a senescent cell may be at least 1-, 2-, 5- or 10-fold high than in the negative control.

The inventors believe that the various senescence cell biomarkers described herein can be harnessed in a cell targeting strategy for specifically targeting and then killing senescent cells.

As such, according to a fourth aspect, there is provided a senescent cell biospecific drug conjugate for killing a senescent cell, the conjugate comprising a senescent cell targeting agent configured, in use, to specifically target and bind to at least one senescent cell biomarker selected from DEP-1, NTAL, EBP50, STX4, VAMP3, ARMCX-3, LANCL1, B2MG, PLD3 and VPS26A, or a variant or fragment thereof, and a cytotoxic agent, which kills the bound senescent cell.

The senescent cell targeting agent may be an antibody or an antigen binding fragment thereof, or an aptamer. Antibodies and fragments thereof represent preferred agents for use according to the invention. Antibodies according to the invention may be produced as polyclonal sera by injecting antigen into animals thereby producing polyclonal antibodies. Preferred polyclonal antibodies may be raised by inoculating an animal (e.g. a rabbit) with antigen using techniques known to the art. Preferably, however, the antibody is a monoclonal antibody. Antibodies according to the invention may also comprise plastic antibodies. The term "plastic antibody" can mean molecularly imprinted polymer nanoparticles (MIPs) with affinity for a target peptide or protein. When monomers are polymerised in the presence of the selected molecular target, collective weak interactions between the monomers and the target during polymerization result in the formation of populations of complementary binding sites in the resulting polymer. This molecular imprinting approach has been previously used to target biologically relevant molecules, including peptides and proteins. Binding affinity and selectivity of MIPs can be comparable to those of natural antibodies and they have previously been shown to be effective in vivo. Moreover, MIPs can be conjugated with the desired cytotoxic drugs and this approach has also been shown to be efficient in the delivery of such toxic payloads to cells.

Preferred antibodies and epitope binding fragments thereof may have immunospecificity for any of the senescence biomarkers according to the invention. Antibodies according to the invention may therefore be raised against any one or more of SEQ ID Nos. 1-19, or a fragment or variant thereof.

Preferably, SEQ ID Nos. 2, 4, 9, 10, 12, 13, 14, 16 or 18, or a fragment or variant thereof may be used as an antigen to create antibodies that specifically bind to senescent cells that display or express an extracellular biomarker according to the invention.

Functionally equivalent derivatives of the antibodies of the invention are also encompassed and may comprise at least 75% sequence identity, more preferably at least 90% sequence identity, and most preferably at least 95% sequence identity. It will be appreciated that most sequence variation may occur in the framework regions (FRs), whereas the sequence of the complementarity determining regions (CDRs) of the antibodies should be most conserved. For introduction into humans, the antibody may be humanised, by splicing V region sequences (e.g. from a monoclonal antibody generated in a non-human hybridoma) with a C region (and ideally FRs from the V region) sequences from human antibodies. The resulting 'engineered' antibodies are less immunogenic in humans than the non-human antibodies from which they were derived and so are better suited for clinical use.

Preferably, the FR region of the antibody is conjugated or fused with the cytotoxic agent, which may comprise a radioisotope, a toxin or a toxic peptide. The isotope may be any one selected from $^{311}$I or $^{90}$Y. The toxin may be doxorubicin, calicheamicin, auristatin, maytansinoid, duocarmycin, or camptothecin analogues. The toxic peptide may be Pseudomonas exotoxin A, diphtheria toxin, ricin, gelonin, saporin or pokeweed an antiviral protein.

Antibodies according to the invention specifically kill senescent cells due to their ability to specifically bind to senescent cells via their CDR region(s). Therefore, the drug conjugate of the fourth aspect, and preferably antibodies according to this aspect, may be use to treat or delay the onset of age-related diseases.

In another embodiment, the targeting agent of the drug conjugate may be a small molecule. The small molecule may be capable of specifically binding to an epitope of a biomarker that is expressed or displayed on the surface of senescent cells. In another embodiment, the small molecule may comprise a means for gaining entry into senescent cells and specifically binding to an epitope of a biomarker that is expressed intracellularly. The small molecule may have a weight of less than 1000 Da.

It will be appreciated that drug conjugates according to this aspect of the invention may be used to specifically target and kill senescent cells that express or display senescent cell biomarkers, according to the invention, on the intracellular or extracellular surface of their plasma membrane.

In embodiments where the drug conjugate is intended to target a biomarker, which is expressed or displayed on the extracellular surface of senescent cells, the targeting agent of the drug conjugate may be an antibody comprising CDRs that specifically binds to an extracellular epitope of the biomarker.

In embodiments where the drug conjugate is intended to target a senescent cell biomarker, which is only expressed intracellularly, the targeting agent of the drug conjugate may be a small molecule that is capable of gaining entry into senescent cells and specifically binding to an epitope of the biomarker.

The senescent cell biomarkers according to the invention may be used to identify senescent cells, which can be targeted, for example, by the drug conjugate according to this aspect of the invention, for treatment of conditions associated with cell senescence, such as ageing and cancer.

Hence, in a fifth aspect, there is provided the senescent cell biospecific drug conjugate according to the fourth aspect, for use as a medicament.

In a sixth aspect, there is provided the senescent cell biospecific drug conjugate according to the fourth aspect, for use in treating, preventing or ameliorating an age-related disease.

In a seventh aspect, there is provided a method of treating, preventing or ameliorating an age-related disease, the method comprising administering, to a subject in need of such treatment, a therapeutically effective amount of the senescent cell biospecific drug conjugate according to the fourth aspect.

Age-related diseases may include but are not limited to impaired wound healing, dermal thinning, arterial wall stiffening, atherosclerosis, cardiovascular disease, cancer, arthritis, glaucoma, cataracts, osteoporosis, type 2 diabetes, hypertension, Alzheimer's disease and other types of dementia.

According to an eighth aspect, there is provided an age-related disease treatment pharmaceutical composition comprising the senescent cell biospecific drug conjugate according to the fourth aspect and a pharmaceutically acceptable vehicle.

According to a ninth aspect, there is provided a method of specifically killing senescent cells, the method comprising:
  (i) determining the presence of a senescence cell in a subject; and
  (ii) administering, to a subject, a therapeutically effective amount of the senescent cell biospecific drug conjugate according to the fourth aspect.

The method of the ninth aspect of the invention may be used to specifically kill senescent cells in vivo, in vitro or ex vivo.

The methods, kits, conjugates and compositions according to the invention preferably comprise the use of at least one of the polypeptide sequences substantially as set out in any one of SEQ ID Nos. 1 to 19, or a fragment or variant thereof, as a biomarker of a senescent cell. Preferably, at least one of the polypeptide sequences substantially as set out in any one of SEQ ID Nos. 2, 4, 9, 10, 12, 13, 14, 16 or 18, or a fragment or variant thereof is used as an extracellular biomarker of senescent cells.

It will be appreciated that agents, conjugates, antibodies and compositions according to the invention may be used in a medicament which may be used in a monotherapy, for treating or delaying the onset of age-related diseases. Alternatively, such agents according to the invention may be used as an adjunct to, or in combination with, known therapies for treating or delaying the onset of age-related diseases.

The agents and antibodies according to the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given.

Medicaments comprising agents and antibodies according to the invention may be used in a number of ways. For instance, oral administration may be required, in which case the agents may be contained within a composition that may, for example, be ingested orally in the form of a tablet, capsule or liquid. Compositions comprising agents of the invention may be administered by inhalation (e.g. intranasally). Compositions may also be formulated for topical use. For instance, creams or ointments may be applied to the skin.

Agents, compositions and antibodies according to the invention may also be incorporated within a slow- or delayed-release device. Such devices may, for example, be inserted on or under the skin, and the medicament may be released over weeks or even months. The device may be located at least adjacent to the treatment site. Such devices may be particularly advantageous when long-term treatment with agents used according to the invention is required and which would normally require frequent administration (e.g. at least daily injection).

In a preferred embodiment, agents, compositions and antibodies according to the invention may be administered to a subject by injection into the blood stream or directly into a site requiring treatment. For example, the medicament may be injected at least adjacent to a senescent cell, or within a tumour. Injections may be intravenous (bolus or infusion) or subcutaneous (bolus or infusion), or intradermal (bolus or infusion).

It will be appreciated that the amount of the agent, composition and antibody that is required is determined by its biological activity and bioavailability, which in turn depends on the mode of administration, the physicochemical properties of the modulator and whether it is being used as a monotherapy or in a combined therapy. The frequency of administration will also be influenced by the half-life of the agent or antibody within the subject being treated. Optimal dosages to be administered may be determined by those skilled in the art, and will vary with the particular agent in use, the strength of the pharmaceutical composition, the mode of administration, and the advancement of the senescence-associated disease(s). Additional factors depending on the particular subject being treated will result in a need to adjust dosages, including subject age, weight, gender, diet, and time of administration.

Generally, a daily dose of between 0.01 µg/kg of body weight and 500 mg/kg of body weight of the agent according to the invention may be used for treating, ameliorating, or preventing senescence-associated disease, depending upon which agent is used. More preferably, the daily dose is between 0.01 mg/kg of body weight and 400 mg/kg of body weight, more preferably between 0.1 mg/kg and 200 mg/kg body weight, and most preferably between approximately 1 mg/kg and 100 mg/kg body weight.

The agent, composition or antibody may be administered before, during or after onset of the senescence-associated disease. Daily doses may be given as a single administration (e.g. a single daily injection). Alternatively, the agent may require administration twice or more times during a day. As an example, agents may be administered as two (or more depending upon the severity of the disease being treated) daily doses of between 25 mg and 7000 mg (i.e. assuming a body weight of 70 kg). A subject receiving treatment may take a first dose upon waking and then a second dose in the evening (if on a two dose regime) or at 3- or 4-hourly intervals thereafter. Alternatively, a slow release device may be used to provide optimal doses of agents according to the invention to a patient without the need to administer repeated doses.

Known procedures, such as those conventionally employed by the pharmaceutical industry (e.g. in vivo experimentation, clinical trials, etc.), may be used to form specific formulations comprising the agents according to the invention and precise therapeutic regimes (such as daily doses of the agents and the frequency of administration).

A "therapeutically effective amount" of agent is any amount which, when administered to a subject, is the amount of the agent, the composition or antibody that is needed to treat the senescence-associated disease, or produce the desired effect, such as inhibiting senescence cell formation.

For example, the therapeutically effective amount of agent used may be from about 0.01 mg to about 800 mg, and preferably from about 0.01 mg to about 500 mg. It is preferred that the amount of agent is an amount from about 0.1 mg to about 250 mg, and most preferably from about 0.1 mg to about 20 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent (e.g. the peptide or antibody) may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidone, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The active agent according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilised by, for example, intramuscular, intrathecal, epidural, intraperitoneal, intravenous and particularly subcutaneous injection. The agent, composition or antibody may be prepared as a sterile solid composition that may be dissolved or suspended at the time of administration using sterile water, saline, or other appropriate sterile injectable medium.

The agents and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The agent, antibody or composition according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

It will be appreciated that the invention extends to any nucleic acid or peptide or variant, derivative or analogue thereof, which comprises substantially the amino acid or nucleic acid sequences of any of the sequences referred to herein, including variants or fragments thereof. The terms "substantially the amino acid/nucleotide/peptide sequence", "variant" and "fragment", can be a sequence that has at least 40% sequence identity with the amino acid/nucleotide/peptide sequences of any one of the sequences referred to herein, for example 40% identity with the polypeptide identified as SEQ ID Nos. 1-19, and so on.

Amino acid/polynucleotide/polypeptide sequences with a sequence identity which is greater than 50%, more preferably greater than 65%, 70%, 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90%, 92%, 95%, 97%, 98%, and most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: END-GAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps but excluding overhangs. Hence, a most preferred to method for calculating percentage identity between two sequences comprises (i) preparing a sequence alignment using the ClustalW program using a suitable set of parameters, for example, as set out above; and (ii) inserting the values of N and T into the following formula:—Sequence Identity=(N/T)*100.

Alternative methods for identifying similar sequences will be known to those skilled in the art. For example, a substantially similar nucleotide sequence will be encoded by a sequence which hybridizes to any sequences referred to herein or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown in SEQ ID Nos.1-19.

Due to the degeneracy of the genetic code, it is clear that any nucleic acid sequence described herein could be varied or changed without substantially affecting the sequence of the protein encoded thereby, to provide a variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine.

Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

Figure 1B:
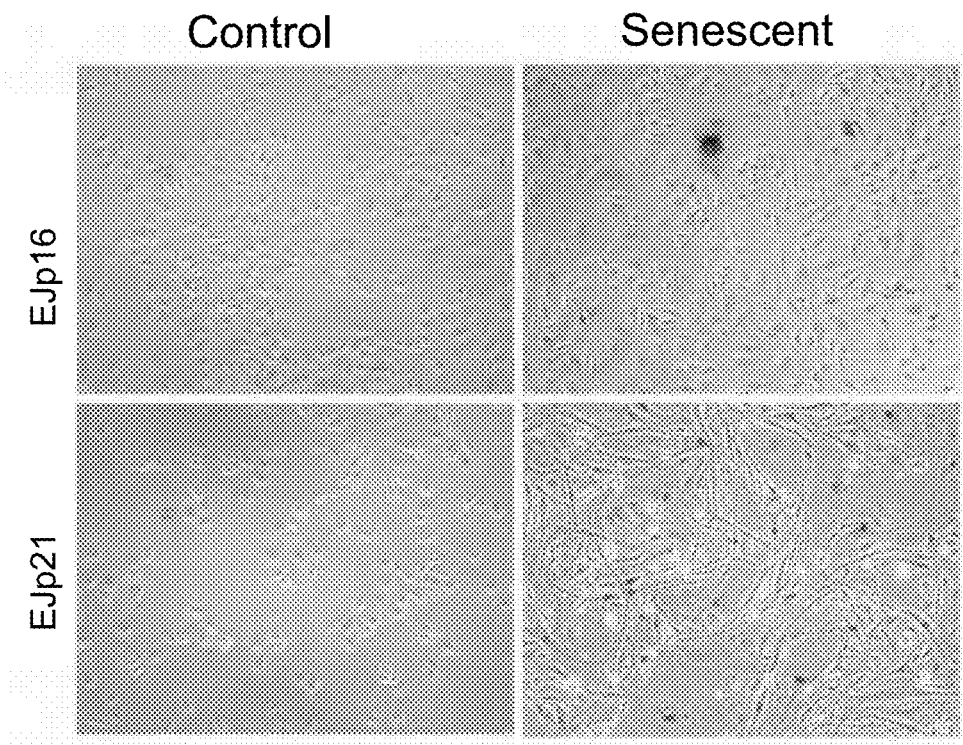
Figure 1C:
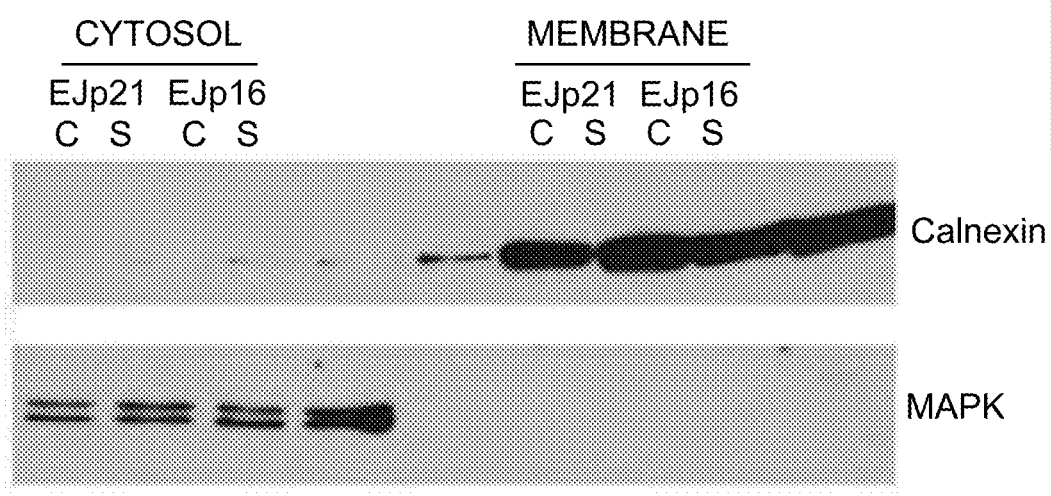
Figure 2A:
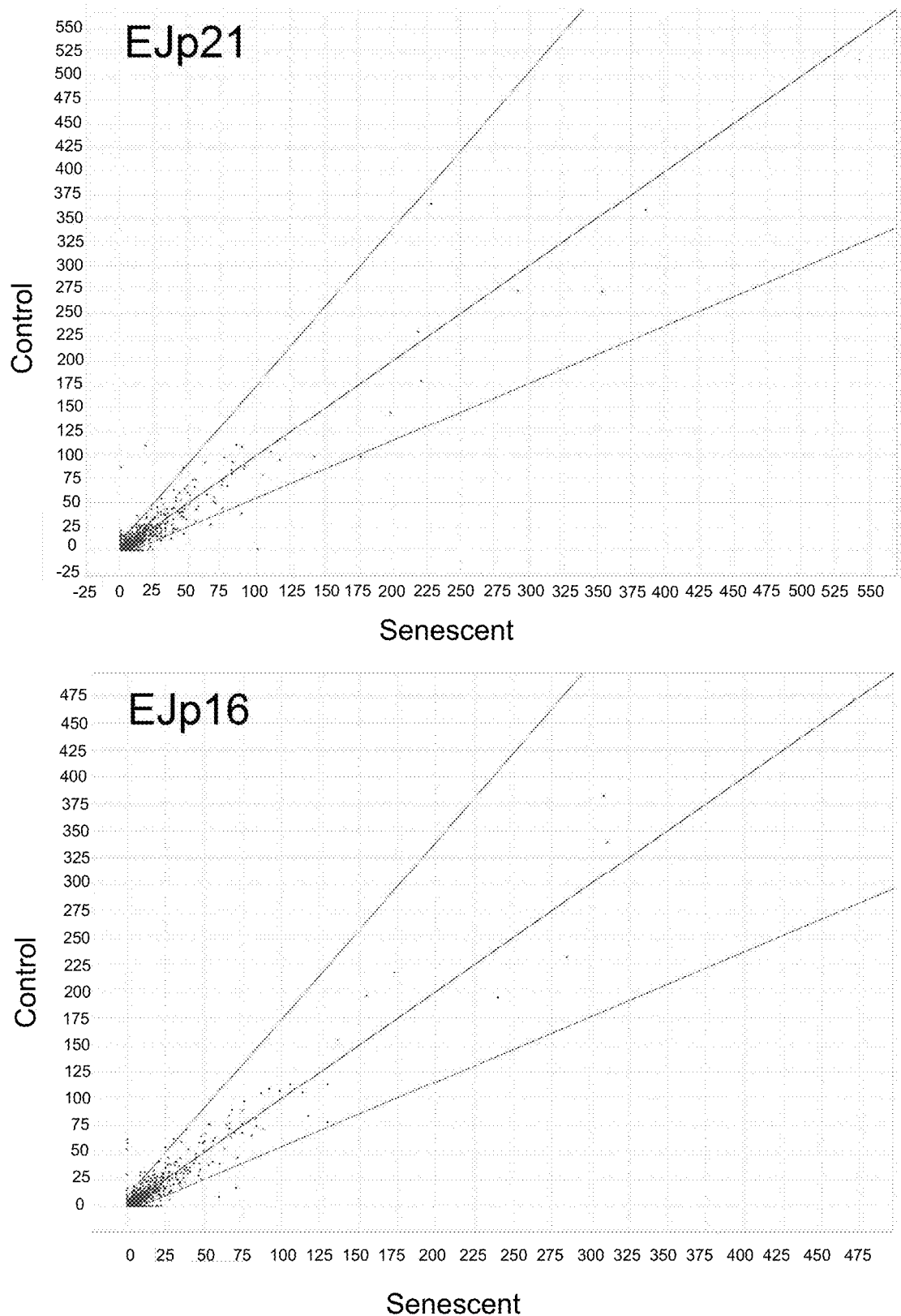
Figure 2B:
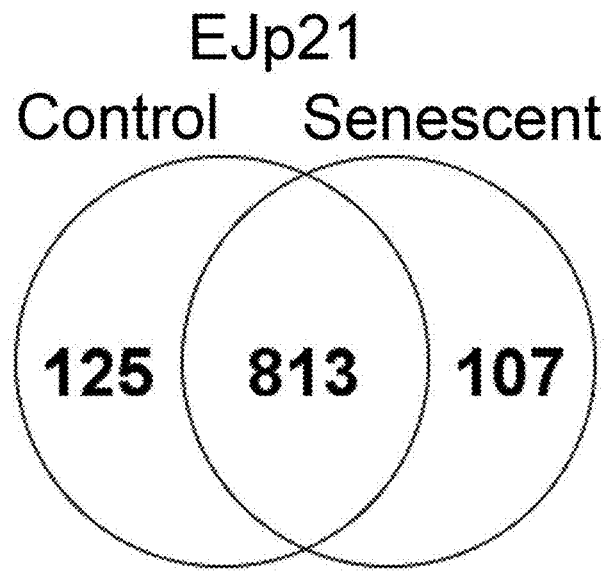

For a better understanding of the invention, and to show how embodiments of the same may be carried into effect, reference will now be made, by way of example, to the accompanying Figures, in which:

FIGS. 1A-1C show the analysis of the membrane fraction of EJp16 and EJp21 cells without and with induction of p16 and p21 respectively. A) Western blots of EJp16 and EJp21 in the presence or absence of tet (tetracycline), showing the induction of expression of exogenous p16 or p21, respectively. B) SA-β-Gal staining of EJp16 and EJp21 cells uninduced (Control) or 4 days after tet removal to induce expression of exogenous p16 or p21 (Senescent). Blue staining and morphological changes are indicative of senescence. C) Western blot analysis of lysates separated into cytosolic and membrane fractions of EJp21 and EJp16 cells uninduced (C) or 4 days after tet removal (S). Calnexin is used as a marker of membrane proteins and MAPK as a marker of the cytosolic fraction;

FIGS. 2A-2B show proteomic screening of membrane proteins in senescent cells. FIG. 2A) Graphic representation of mass spec hits in EJp21 and EJp16 control and senescent cells. FIG. 2B) Number of membrane proteins differentially expressed in control and senescent EJp21 and EJp16, compared to those present in both conditions.

Figure 3A:
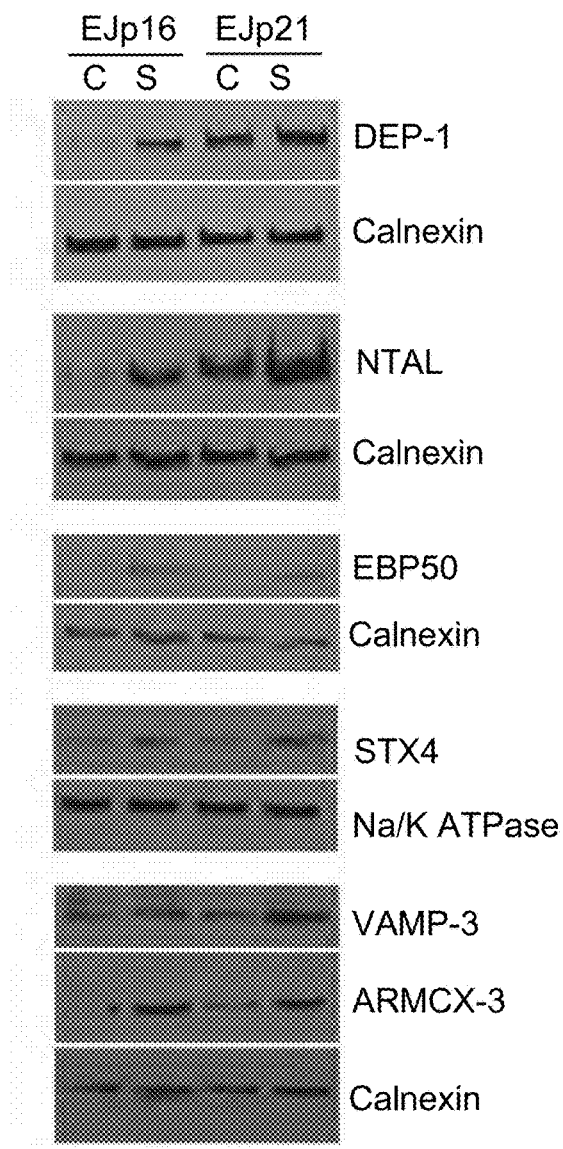
Figure 3B:
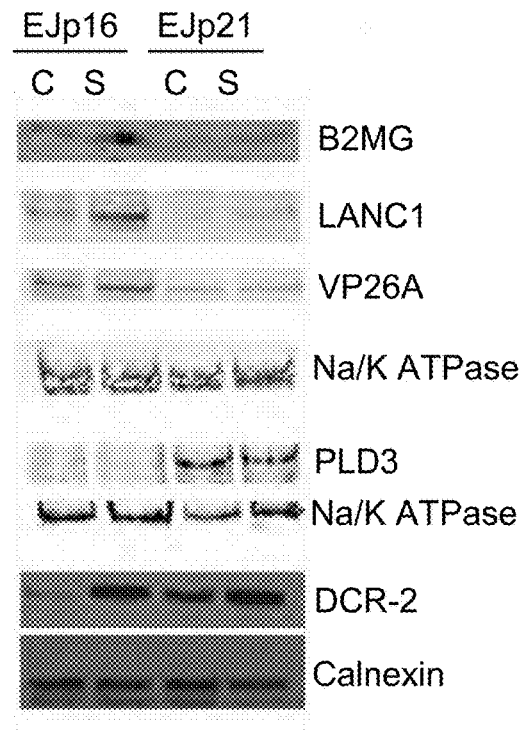
Figure 4:
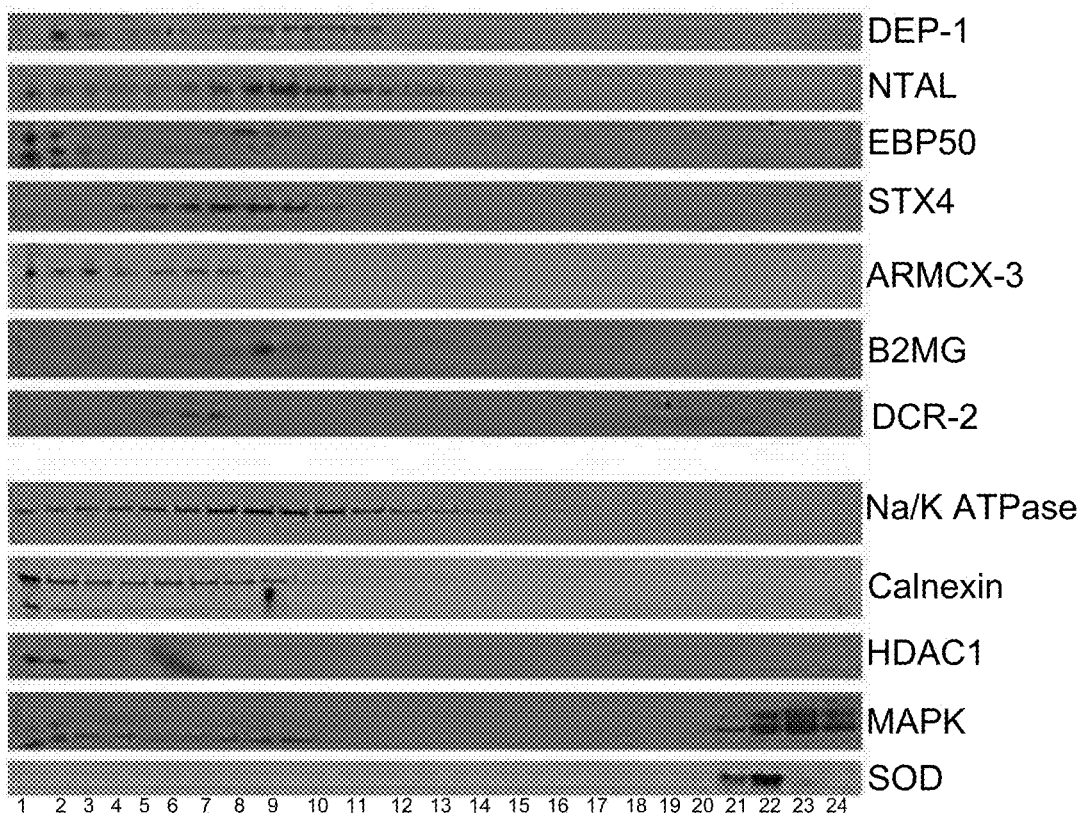
Figure 5:
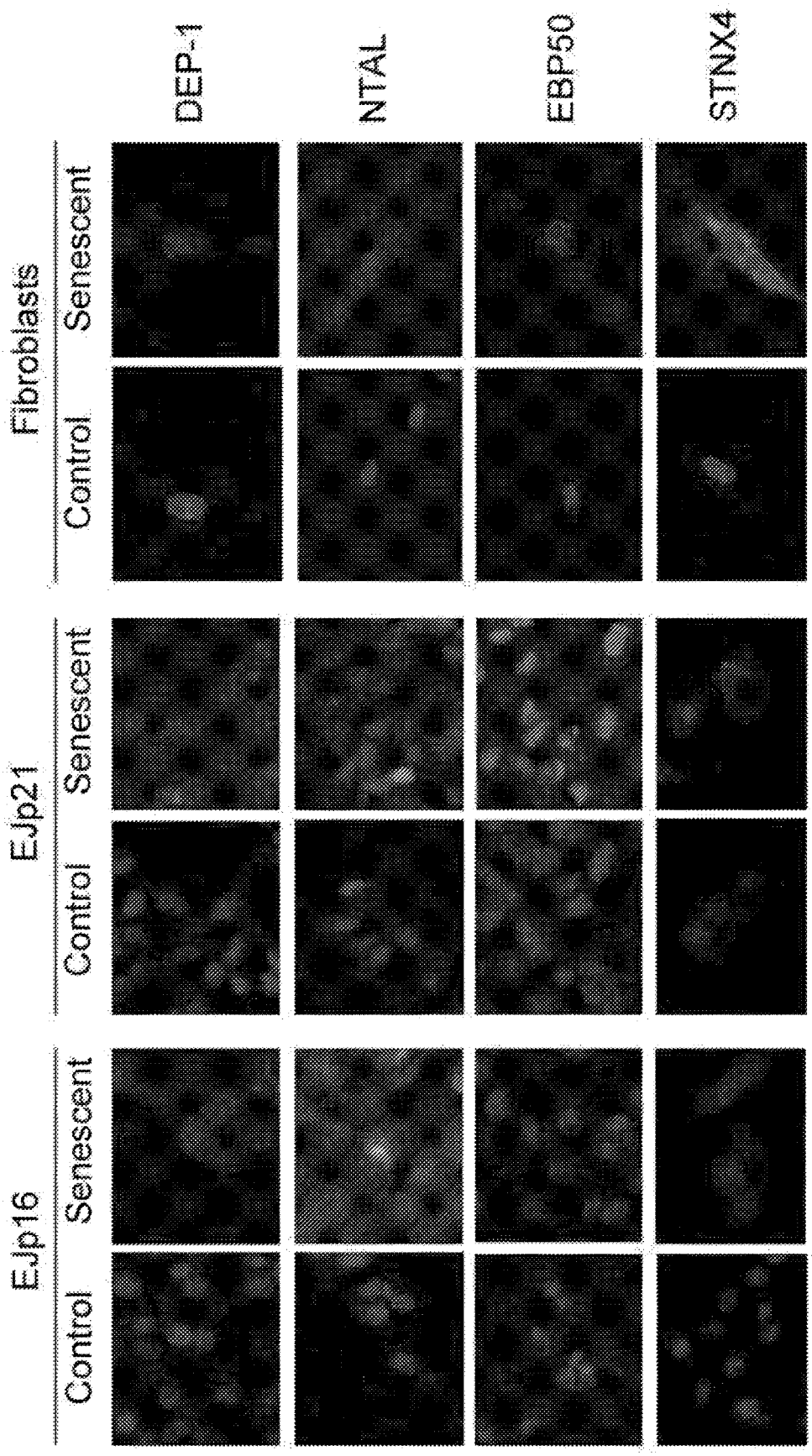
Figure 5:
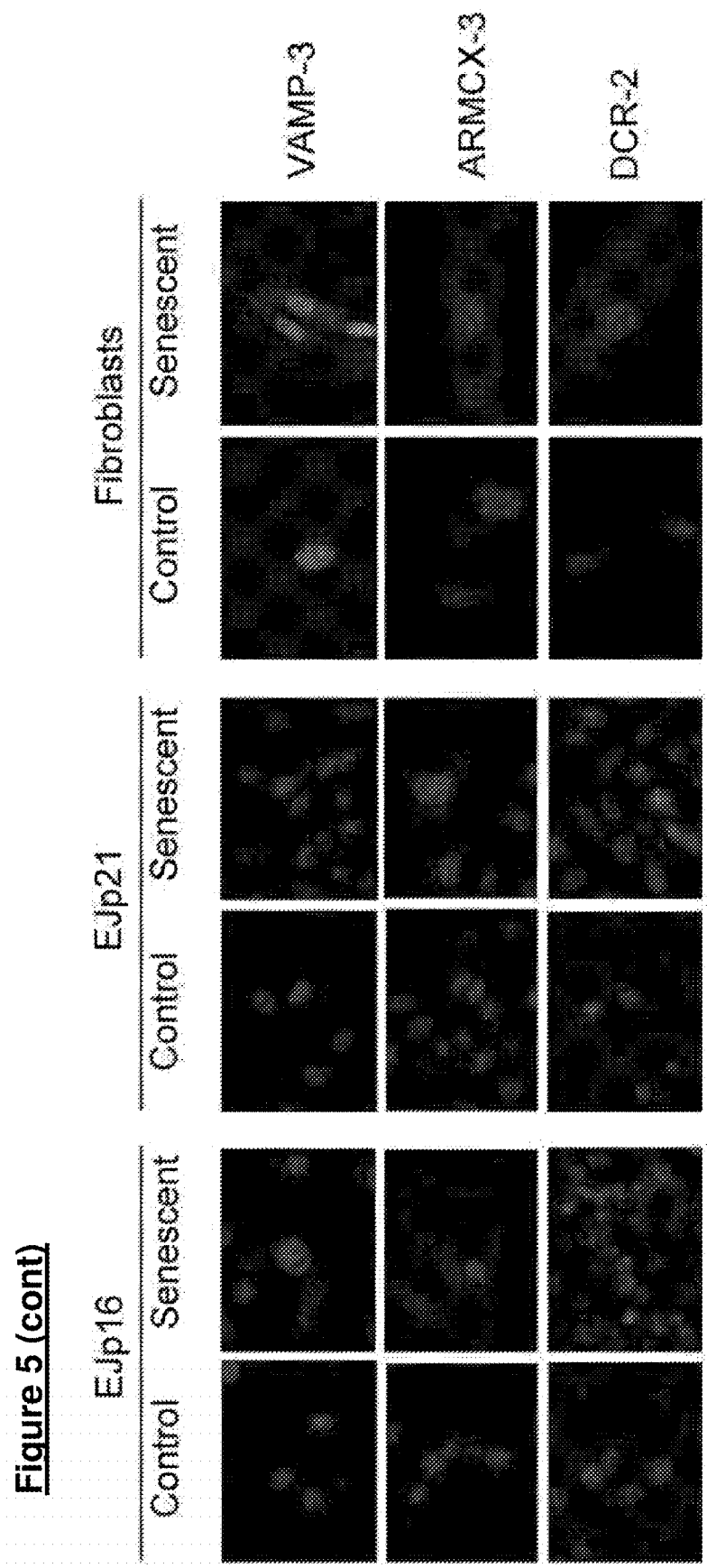
Figure 6A:
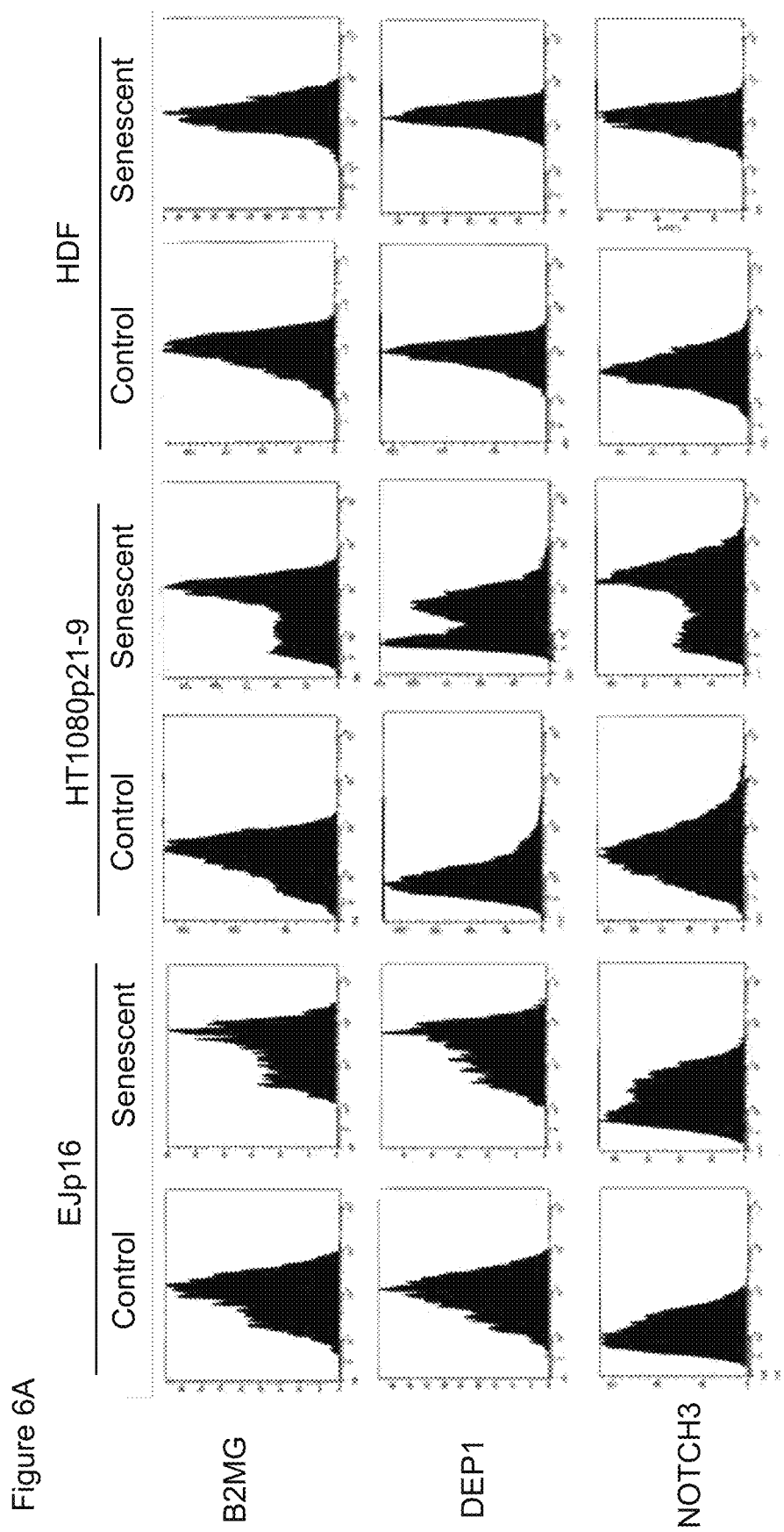
Figure 6B:
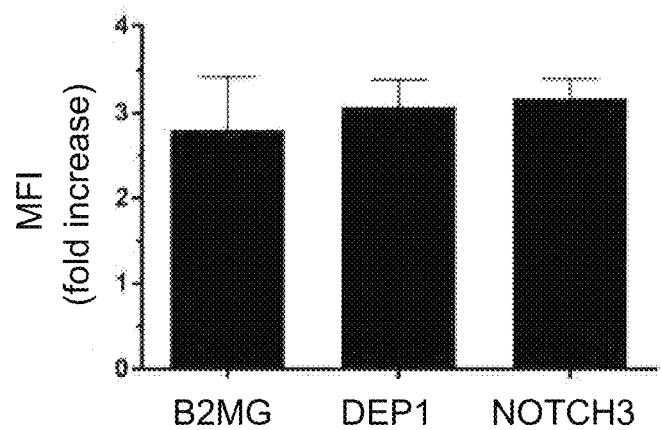
Figure 6B:
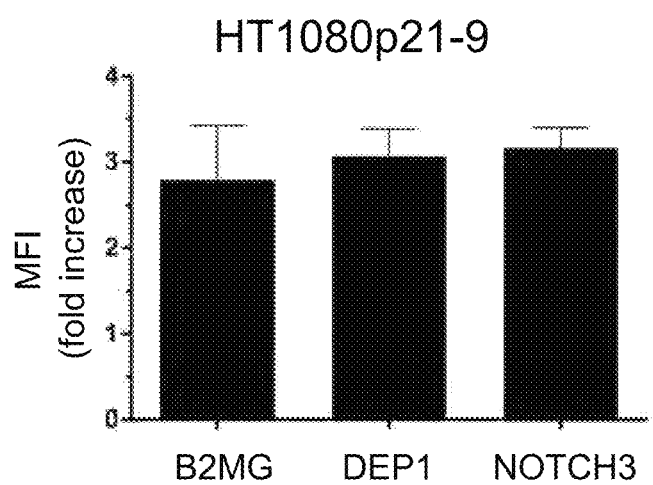
Figure 6B:
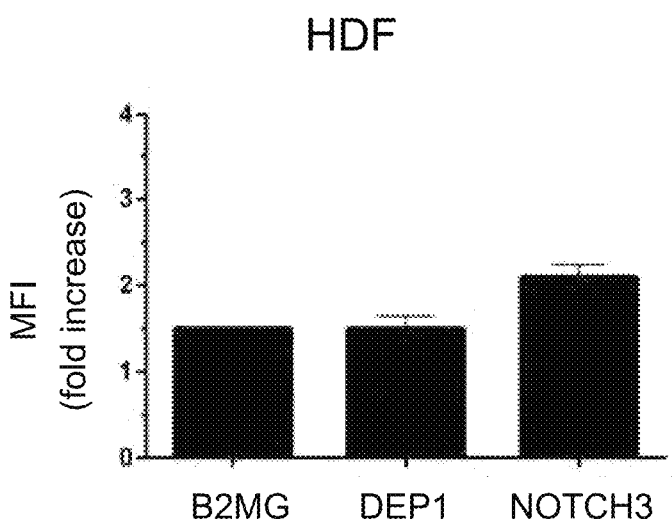
Figure 7:
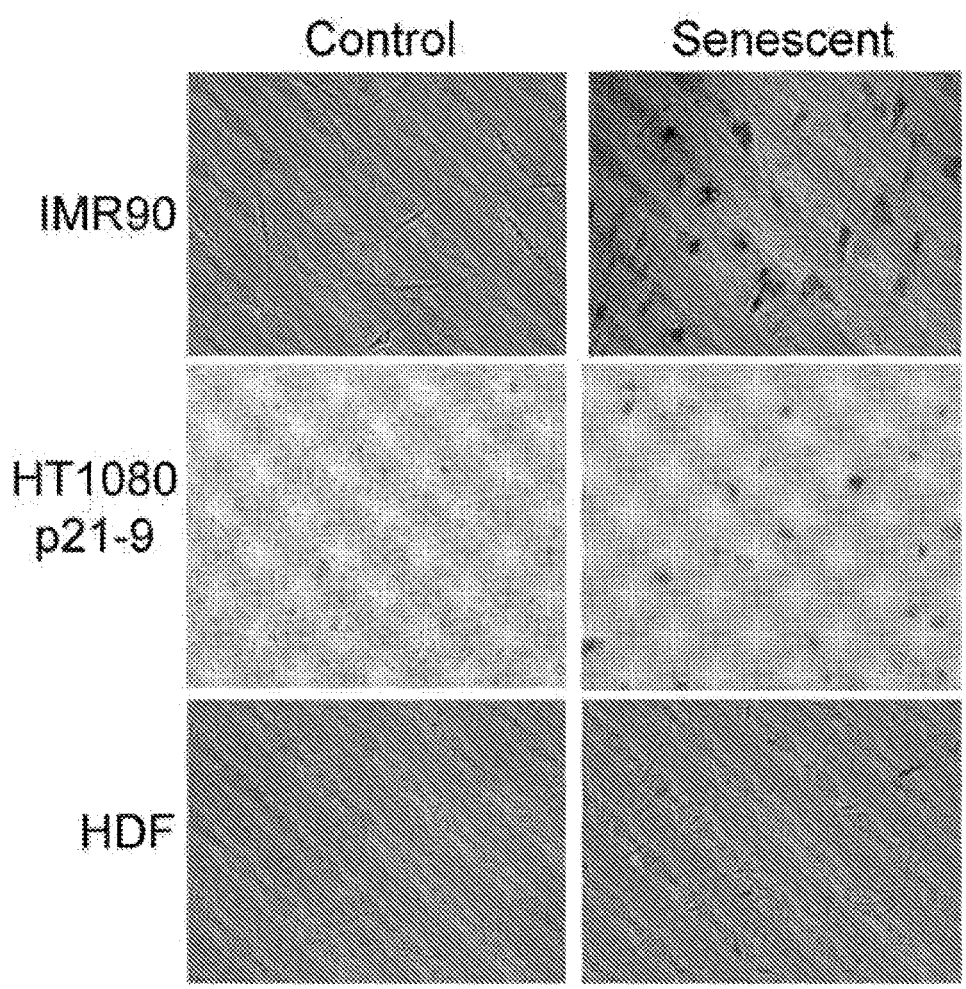

FIGS. 3A and 3B are Western Blot validation of senescent-specific targets. FIG. 3A) and FIG. 3B) show protein expression of selected targets in the membrane fraction of lysates from EJp16 and EJp21 uninduced (C) or 4 days after tet removal (S). Calnexin and Na/K ATPase are used as loading controls;

FIG. 4 shows the expression of selected targets in membranes of senescent cells. Sucrose gradient fractionation of the membrane fraction of lysates from EJp16 4 days after tet removal. Calnexin and Na/K ATPase are used as markers of the cell membrane fractions. HDAC1 is used as marker of the nuclear fraction. MAPK is used as marker of the cytosolic fractions. SOD is used as marker of the mitochondrial fraction;

FIG. 5 shows the expression and localization of the novel senescence markers. Immunofluorescent images of selected targets in EJp16 and EJp21 uninduced (Control) or 4 days after tet removal (Senescent), as well as early passage normal human diploid fibroblasts compared to those entering replicative senescence;

FIGS. 6A and 6B relate to defining a new protocol for the detection of senescent cells. FIG. 6A) Representative plot analysis of fluorescence levels in control and senescent EJp16, HT1080p21-9 and human diploid fibroblasts (HDF) stained with fluorescently tagged antibodies against B2MG, DEP-1 and NOTCH3, as measured by flow cytometry. Senescent cells were analysed after 5 days of p16 or p21 expression. FIG. 6B) Average fold increases of mean fluorescence intensity (MFI) of the same cells. Experiments were performed in triplicate. Error bars show standard deviation; and FIG. 7 is SA-β-Gal staining of control and senescent IMR90, HT1080p21-9 (after 4 days of p21 expression following exposure to IPTG) and normal human diploid fibroblasts (HDF).

EXAMPLES

The inventors have studied the expression profile of plasma membrane proteins in senescent cells in order to identify novel markers that could be easily recognized and propose potential effectors and modulators of the senescent pathway. Ten novel specific markers of senescence were validated (Examples 1 and 2), and two of these were selected in order to develop a fast and straightforward FACS-based approach to identify senescent cells (Example 3).

Materials and Methods

Cell Culture

The EJ human bladder cancer cell lines were maintained in DMEM supplemented with 10% fetal bovin serum (FBS) (Gibco), and pen-strep (50 unit/ml). EJ p21 and EJp53 cells were maintained with hygromycin (100 μg/ml) and genticin (750 μg/ml) plus (1 μg/ml) tetracycline. EJp16 cells were maintained with hygromycin (100 μg/ml) and puromycin (2 μg/ml) plus (1 μg/ml) tetracycline. In order to inhibit p21 and p16 expression, tetracycline (tet) was added to the medium every 3 days to final concentration (1 μg/ml). To induce p21, p16 and p53 expression, cells were washed three times and seeded directly in culture medium in the absence of tet (Fang et al., 1999). IMR90 (human fibroblasts wad derived from lungs of a 16-weeks female fetus) and 501T (human fibroblast which is driven from normal human skin) these fibroblasts were cultured until they reached the end of their replicative senescence. Restrictive dermopathy (RD) cells were kindly provided by Dr Sue Shackleton. To induce p21 expression in HT1080p21, 100 μM IPTG was added to the medium.

Plasma Membrane Protein Extraction

This method was performed according to the Abcam Plasma Membrane Protein extraction Kit (ab65400).

SDS-PAGE Separation

Senescent and growing EJp21 and EJp16 plasma membrane samples were separated by 10% SDSPAGE. After staining with the Coomassie blue, the gel was cut to obtain separate sample lanes. Each gel strip was then sliced into 50 slices, from the loading well down to the bottom of the gel. The proteins in the gel bands were digested with trypsin according to the protocol described previously (Shevchenko et al, 2006).

Extraction and Analysis of Proteins from Gel Lanes by Mass Spectrometry (Synapt G2S).

Gel lanes were cut sequentially into slices of approximately 1.5 mm and transferred to a 96 well low binding PCR plate. Each slice was washed/swollen with ammonium bicarbonate (80 ul, 50 mM) for 30 minutes, after this time the buffer was aspirated off using a Gilson. Each slice was destained with acetonitrile (80 ul) for 30 minutes, the solvent was removed. Steps 2) and 3) were repeated. After aspiration of the final acetonitrile, 15 ul of sequencing grade modified trypsin V5111 (Promega), 20 ug/1.8 ml 25 mM ammonium bicarbonate, was added to each dehydrated gel piece.

The plate was sealed and heated at 30° C. overnight. The sealing film was removed and extraction buffer added to each well (80 μl, 97% TFA (0.2%) 3% acetonitrile). The samples were extracted at room temperature for 1 hour. The extracted samples were transferred to low-binding eppendorf tubes and concentrated to dryness in a speedvac. The samples were redissolved in injection solvent (40 ul, 5% TFA) and analysed by mass spectrometry. Nanoscale LC was used to separate the complex peptide mixtures using a Waters nanoACQUITY UPLC. Chromatography was performed using a 50 minute reversed phase gradient (formic acid (0.1%)/acetonitrile) and a 75 μm×25 cm C18 column (Waters, BE130) operated at 300 nL/min. Mass spectrometry analysis was performed using a SYNAPT G2S (Waters Manchester UK) operated in a data-independent (MSE) manner. The selected analysis mode enabled precursor and fragment ions from the tryptic digest to be analysed simultaneously. The data acquired was processed and searched using ProteinLynx Global Server (Waters) and visualized and reanalyzed using Scaffold (Proteome Software, Oregon, USA).

Senescence-Associated-β-Galactosidase (SA-β-Gal) Staining

Cells were washed three times with PBS, and fixed with 4% formaldehyde for 5 min at room temperature. The detail of SA-β-gal staining was described previously (Dimri et al, 1995).

Immunoblot Analysis

Extracellular membrane samples were extracted and 1 μg/ml Protease Inhibitor Cocktail Set III (Calbiochem) added to the samples. Protein concentrations were then determined using Bradford protein assay (Fermentas). 20 μg of total cell protein per sample were subjected to 10% or 6% SDS-PAGE and transferred to Immobilon-P membrane (Millipore). An ECL detection system (Thermo Scientific) was used.

Immunofluorescence

Cells were split into 6-well plates containing sterile coverslips. After 24 hours, media was aspirated from the plates and cells were washed three times with 1×PBS. Cells were fixed using 1 ml of 4% paraformaldehyde for 30 min with gentle shaking. After fixing, cells were washed three times with 1×PBS and permeabilised with 1 ml 0.1% Triton X-100 for 10 minutes. Cells were then washed three times with 1×PBS and blocked with 1% BSA for 30 minutes. Coverslips were incubated with 100 μl 1:100 primary antibody overnight at 4° C. The following day, coverslips were washed three times with 1×PBS and incubated with 100 μl secondary anti-rabbit and anti-mouse antibody (Alexa Fluor 488 and 594, Invitrogen) for 45 minutes in the dark. After incubation, coverslips were washed three times with 1×PBS and stained with 4',6-Diamidino-2-Phenylindole, Dihydrochloride (DAPI, Invitrogen) for 10 minutes. Slides were labelled and the coverslips were mounted and sealed with transparent nail varnish. Slides were analysed using a Nokia TE300 semi-automatic microscope.

FACS Analysis

Plates were washed with cold 1×PBS, and then the cells were collected by gently scraping them in 0.5 ml cold 1×PBS on ice. Trypsin should not be used because it leads to loss of extracellular proteins. The cells were then spun down at 200 g for 5 min at 4° C. The supernatant was discarded, the cells were re-suspend in 2001 of blocking buffer (0.5% BSA+1×PBS) and then they were incubated on ice for 15 min. The cells were transferred into a 96 rounded bottom multi-well plate and spun down at 500 g for 5 min at 4° C. Once again, the supernatant was discarded. The pellet was re-suspend in an Antibody Mix and incubated at 4° C. in the dark for 30-45 min. The cells were then washed twice with Blocking Buffer (150 µl per well) followed by a spin at 500 g for 5 min at 4° C. The supernatant was discarded and the pellet was re-suspended in 300-500l of Blocking Buffer. Cellular fluorescence was detected using a cytometer.

Figure 2B:
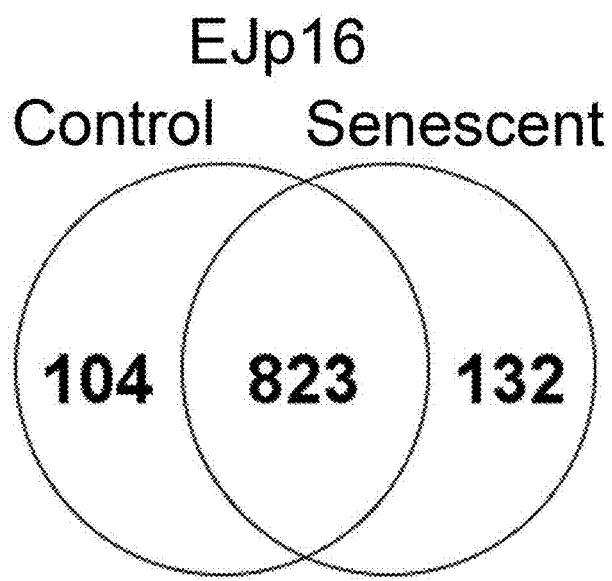

Example 1—Proteomic Analysis of the Expression of Membrane Proteins in Senescent Cells In order to characterize the profile of proteins selectively expressed in the plasma membrane of senescent cells, the inventors used a bladder cancer cell line, EJ, with a tet-regulatable p21 or p16 expression system (see FIG. 1A). These cells, named EJp21 and EJp16, respectively (Fang et al, 1999; Macip et al, 2002), irreversibly senesce after prolonged expression of the induced protein (see FIG. 1B). The membrane fraction was isolated form lysates of these proteins (see FIG. 1C) and a mass spectrometry screen performed to compare the senescent cells to their non-senescent counterparts. As shown in FIG. 2, 107 proteins were exclusively present in membranes of senescent EJp21 and 132 in EJp16. From these lists, ten proteins were selected for further validation: DEP-1, NTAL, EBP50, STX4, VAMP-3, ARMX-3, B2MG, LANCL1, VPS26A and PLD3. They were all chosen because they had not previously been shown to be associated with senescence and are all plasma membrane-associated proteins. None of the selected proteins had known functions that could immediately predict their mechanistic involvement in the senescent pathway. Of note, the screen also detected DCR-2, Notch-3 and ICAM1, all of which had been previously associated with senescence, which confirms the suitability of the screening protocols used.

Example 2—Validation of Potential Membrane Markers of Senescent Cells

The inventors next confirmed that the ten selected proteins (listed in Example 1) were indeed expressed preferentially in the membranes of senescent cells. To this end, the cell membrane fraction of lysates from EJp16 and EJp21 that had been induced to senesce were used. As shown in FIG. 3A, basal levels of DEP-1, NTAL, EBP50, STX4, VAMP3 and ARMCX-3 were low in uninduced EJp16 cells. After 5 days of p16 expression, when cells are known to be irreversibly senescent (Macip et al, 2002), expression of these proteins was highly increased, except for STX4 and VAMP-3, which only showed a minor induction. DEP-1 and NTAL were notably expressed in EJp21 in basal conditions, but were still up-regulated after the p21 induction for 5 days. NTAL, EBP50, STX4, VAMP-3 and ARMCX-3 all had low basal levels and a substantial increase in expression after EJp21 entered senescence. As shown in FIG. 3B, B2MG, LANCL1 and VPS26A underwent moderate increases in response to p16, but not p21. Also, PLD3 did not show any expression change in any model tested. Finally, DCR-2 was shown to be induced in both p16- and p21-dependent senescence, as expected. All of these results together confirmed that five of the potential markers (DEP-1, NTAL, EBP50, STX4, VAMP-3 and ARMCX-3) were specifically expressed in senescent cells, although at different levels, and three more (B2MG, LANCL1 and VPS26A) were up-regulated only in p16-induced senescence.

The inventors further confirmed these results using cell fractionation of EJp16 cell lysates by sucrose gradient. FIG. 4 shows that DEP-1, NTAL, EBP50, STX4, ARMCX-3 and B2MG co-localize in the same fraction as cell membrane markers Na/K ATPase and Calnexin. This underscores the hypothesis that these proteins are present in membrane of senescent cells. Immunofluorescent microscopy was also used to study the expression and localization of these proteins (see FIG. 5). DEP-1, NTAL, EBP50 and STX4 showed induction in senescent EJp16, as compared to the positive control (DCR-2). VAMP-3 and ARMCX-3 also showed up-regulation, but at lower levels. In EJp21, all markers were significantly increased. The expression of these proteins in IMR90 human fibroblasts was also measured, comparing early passage cells to those induced to senesce after serial passaging (see FIG. 7). All the proteins tested showed low basal levels in growing fibroblasts and increased expression in senescent ones (see FIG. 5), confirming that they could be used as markers of replicative senescence in normal cells.

Example 3—Characterization of Senescence Markers by FACS Analysis

With the information from the validation experiments (i.e. Example 2), the inventors chose two of the novel membrane proteins (DEP-1 and B2MG) to define a simple and specific protocol, using flow cytometry, that would allow for the rapid detection of senescent cells in culture. DEP-1 and B2MG were initially chosen because they had large extracellular epitopes recognized by commercially available fluorescent-tagged antibodies. NOTCH3 was used as a positive control. All three antibodies were mixed and incubated with non-permeabilized cells (see Materials and Methods for protocol details). The total time needed to measure the presence of senescent cells in cell cultures was under 2 hours. As shown in FIG. 6, there was a consistent 2- to 3-fold increase in all of the markers in EJp16 after the induction of senescence. This result was confirmed using another model of p21-induced senescence HT1080p21-9 (Chang et al, 2000; Masgras et al, 2012) (see FIG. 7), which showed approximately a 3-fold increase in cell surface expression in each of the three markers. Moreover, normal human diploid fibroblasts that entered replicative senescence also showed up-regulation of the markers, although at lower levels (FIG. 6), which is consistent with a lower percentage of SA-$\beta$-Gal positive cells (see FIG. 7). These results confirm that the validated membrane markers of senescence from the inventors proteomic screen can be successfully used to determine the presence of senescent cells in culture and could provide a faster and more selective detection tool than those currently available.

DISCUSSION

Senescence is a well-defined cellular mechanism with a critical role in processes as diverse as cancer and ageing. Despite having been studied for decades, the mechanisms involved in senescence are not fully understood. One of the features of senescent cells that had not been previously characterized was the profile of expression of proteins on their surface. Such proteins have the potential to be especially relevant for three reasons. Firstly, these proteins could contribute to explaining how these cells interact with the microenvironment and also aid our understanding of the mechanisms of senescent cell clearance. This is important in the context of the tumour suppressor functions of senescence as well as its involvement in the symptoms associated with ageing (Baker et al, 2011). Secondly, specific cell membrane proteins with extracellular epitopes would be useful for rapidly detecting senescent cells in a laboratory environment. Given that the current protocols for these analyses are far from ideal, identifying extracellular epitopes of the senescent proteome could greatly improve this field of study. Finally, uncovering novel up-regulated proteins could enhance our understanding of the processes that determine the establishment and maintenance of the senescent phenotype.

Using a proteomics approach, the inventors identified and validated ten proteins expressed at higher levels in plasma membrane fractions of senescent cells than in controls. Six of the proteins have at least one extracellular domain or are associated with the plasma membrane. From their known functions, it is not immediately clear what role they could play in senescence. DEP-1 participates in cell adhesion, which could determine how senescent cells interact with their microenvironment. STX4 and VAMP-3 contribute to vesicle traffic in cells, perhaps impinging on some aspects of the SASP. NTAL, EBP50 and LANCL1 belong to different signalling pathways that could be linked to senescence. B2MG and VPS26A have roles in the immune system, and this could be related to the clearance of senescent cells from tissues. ARMCX-3 has a potential tumour suppressor effect that could perhaps be explained by its role in inducing senescence. Finally, PLD3's phospholipase activity may be involved in senescence through unknown mechanisms. Further experiments to determine whether any of these proteins actively contribute to the senescent phenotype (or if their upregulation is just an epiphenomenon) are currently being performed.

All 10 targets were studied in different models, mainly the inducible EJ cell lines that undergo senescence through activation of one of the main pathways involved in the process, p16 or p21. All of them were up-regulated in at least one of the models, with most clearly induced in both. Moreover, the results were also validated in normal human fibroblasts, thus confirming the relevance of the data in both replicative and stress-induced models of senescence.

The inventors have proven that these proteins, specifically the six that showed better induction (DEP-1, NTAL, EBP50, STX4, VAMP-3, ARMCX-3 and B2MG), have the potential to be used as surrogate markers of senescence, together with those previously described (p21, p16, p15, DCR2, NOTCH-3, etc.). As a proof of principle, they selected two of the six proteins, DEP-1 and B2MG, to develop a staining protocol that could help determine the amount of senescent cells present in a sample. The goal was to achieve higher specificity and shorter experimental times than the current gold standard, the SA-β-Gal assay. The inventors believe that their results show that such a detection method, based on specific antibodies against extracellular epitopes, is feasible and successful. Results can be obtained under 2 hours, compared with the overnight incubation times needed for the classic SA-β-galactosidase staining. Further optimization will be required to determine the best targets and conditions. Increasing to the simultaneous number of markers detected could augment the specificity of the protocol, if needed. Also, markers more specific to either the p16 or p21 pathways could help determine which of the two pathways is preferentially activated in response to each senescence-inducing stimulus.

This proteomic screen provides new information about the mechanisms involved in senescence and can be used experimentally to rapidly detect senescent cells. Moreover, the inventors hope that further studies, in the future, will determine the exact role of these novel markers in the senescent pathways, thus contributing to our understanding of this intricate cellular process. Such information could be important to define new therapeutic interventions that could increase the positive impact of senescence on human health and/or diminish its negative effects.

REFERENCES

Baker D J, Wijshake T, Tchkonia T, LeBrasseur N K, Childs B G, van de Sluis B, Kirkland J L, van Deursen J M (2011) Clearance of p16Ink4a-positive senescent cells delays ageing associated disorders. *Nature* 479: 232-236.

Campisi J, d'Adda di Fagagna F (2007) Cellular senescence: when bad things happen to good cells. *Nature reviews Molecular cell biology* 8: 729-740.

Castro M E, Ferrer I, Cascon A, Guijarro M V, Lleonart M, Ramon y Cajal S, Leal J F, Robledo M, Carnero A (2008) PPP1CA contributes to the senescence program induced by oncogenic Ras. *Carcinogenesis* 29: 491-499.

Chang B D, Broude E V, Fang J, Kalinichenko T V, Abdryashitov R, Poole J C, Roninson I B (2000) p21Waf1/Cip1/Sdi1-induced growth arrest is associated with depletion of mitosiscontrol proteins and leads to abnormal mitosis and endoreduplication in recovering cells. *Oncogene* 19: 2165-2170.

Chen Z, Trotman L C, Shaffer D, Lin H K, Dotan Z A, Niki M, Koutcher J A, Scher H I, Ludwig T, Gerald W, Cordon-Cardo C, Pandolfi P P (2005) Crucial role of p53-dependent cellular senescence in suppression of Pten-deficient tumorigenesis. *Nature* 436: 725-730.

Collado M, Gil J, Efeyan A, Guerra C, Schuhmacher A J, Barradas M, Benguria A, Zaballos A, Flores J M, Barbacid M, Beach D, Serrano M (2005) Tumour biology: senescence in premalignant tumours. *Nature* 436: 642.

Collado M, Serrano M (2010) Senescence in tumours: evidence from mice and humans. *Nature reviews Cancer* 10: 51-57.

Dankort D, Filenova E, Collado M, Serrano M, Jones K, McMahon M (2007) A new mouse model to explore the initiation, progression, and therapy of BRAFV600E-induced lung tumors. *Genes & development* 21: 379-384.

Dimri G P, Lee X H, Basile G, Acosta M, Scott C, Roskelley C, Medrano E E, Linskens M, Rubelj I, Pereirasmith O, Peacocke M, Campisi J (1995) A Biomarker That Identifies Senescent Human-Cells in Culture and in Aging Skin in-Vivo. *Proceedings of the National Academy of Sciences of the United States of America* 92: 9363-9367.

Drummond-Barbosa D (2008) Stem Cells, Their Niches and the Systemic Environment: An Aging Network. *Genetics* 180: 1787-1797.

Fang L, Igarashi M, Leung J, Sugrue M M, Lee S W, Aaronson S A (1999) p21Waf1/Cip1/Sdi1 induces permanent growth arrest with markers of replicative senescence in human tumor cells lacking functional p53. *Oncogene* 18: 2789-2797

Hayflick L, Moorehead P (1961) The serial cultivation of human diploid strains. *Exp Cell Res* 25: 585-621.

Hoshino Y, Koide H, Urakami T, Kanazawa H, Kodama T, Oku N and Shea K J (2010) Recognition, Neutralization, and Clearance of Target Peptides in the Bloodstream of Living Mice by Molecularly Imprinted Polymer Nanoparticles: A Plastic Antibody. *J. Am Chem Soc* 132: 6644-6645.

Kondoh H, Lleonart M E, Gil J, Wang J, Degan P, Peters G, Martinez D, Carnero A, Beach D (2005) Glycolytic enzymes can modulate cellular life span. *Cancer research* 65: 177-185.

Kosar M, Bartkova J, Hubackova S, Hodny Z, Lukas J, Bartek J (2011) Senescenc-eassociated heterochromatin foci are dispensable for cellular senescence, occur in a cell type and insult-dependent manner and follow expression of p16(ink4a). *Cell cycle* 10: 457-468.

Kuilman T, Michaloglou C, Mooi W J, Peeper D S (2010) The essence of senescence. *Genes & development* 24: 2463-2479.

Lee B Y, Han J A, Im J S, Morrone A, Johung K, Goodwin E C, Kleijer W J, DiMaio D, Hwang E S (2006) Senescence-associated beta-galactosidase is lysosomal beta-galactosidase. *Aging Cell* 5: 187-195.

Lowe S W, Cepero E, Evan G (2004) Intrinsic tumour suppression. *Nature* 432: 307-315.

Macip S, Igarashi M, Berggren P, Yu J, Lee S W, Aaronson S A (2003) Influence of induced reactive oxygen species in p53-mediated cell fate decisions. *Molecular and cellular biology* 23: 8576-8585.

Macip S, Igarashi M, Fang L, Chen A, Pan Z Q, Lee S W, Aaronson S A (2002) Inhibition of p21-mediated ROS accumulation can rescue p21-induced senescence. *The EMBO journal* 21: 2180-2188.

Majumder P K, Grisanzio C, O'Connell F, Barry M, Brito J M, Xu Q, Guney I, Berger R, Herman P, Bikoff R, Fedele G, Baek W K, Wang S, Ellwood-Yen K, Wu H, Sawyers C L, Signoretti S, Hahn W C, Loda M, Sellers W R (2008) A prostatic intraepithelial neoplasiadependent p27 Kipi checkpoint induces senescence and inhibits cell proliferation and cancer progression. *Cancer cell* 14: 146-155.

Mantovani A (2004) Chemokines in neoplastic progression. *Seminars in cancer biology* 14: 147-148 17.

Masgras I, Carrera S, de Verdier P J, Brennan P, Majid A, Makhtar W, Tulchinksy E, Jones G D, Roninson I B, Macip S (2012) Reactive oxygen species and mitochondrial sensitivity to oxidative stress determine induction of cancer cell death by p21. *The Journal of biological chemistry*.

Michaloglou C, Vredeveld L C, Soengas M S, Denoyelle C, Kuilman T, van der Horst C M, Majoor D M, Shay J W, Mooi W J, Peeper D S (2005) BRAFE600-associated senescence-like cell cycle arrest of human naevi. *Nature* 436: 720-724.

Narita M, Narita M, Krizhanovsky V, Nunez S, Chicas A, Hearn S A, Myers M P, Lowe S W (2006) A novel role for high-mobility group a proteins in cellular senescence and heterochromatin formation. *Cell* 126: 503-514.

Narita M, Nunez S, Heard E, Narita M, Lin A W, Hearn S A, Spector D L, Hannon G J, Lowe S W (2003) Rb-mediated heterochromatin formation and silencing of E2F target genes during cellular senescence. *Cell* 113: 703-716.

Sarkisian C J, Keister B A, Stairs D B, Boxer R B, Moody S E, Chodosh L A (2007) Dose-dependent oncogene-induced senescence in vivo and its evasion during mammary tumorigenesis. *Nature cell biology* 9: 493-505.

Serrano M, Lin A W, McCurrach M E, Beach D, Lowe S W (1997) Oncogenic ras provokes premature cell senescence associated with accumulation of p53 and p16INK4a. *Cell* 88: 593-602.

Shevchenko A, Tomas H, Havlis J, Olsen J V, Mann M (2006) In-gel digestion for mass spectrometric characterization of proteins and proteomes. *Nature protocols* 1: 2856-2860.

Wang W, Chen J X, Liao R, Deng Q, Zhou J J, Huang S, Sun P (2002) Sequential activation of the MEK-extracellular signal-regulated kinase and MKK3/6-p38 mitogen-activated protein kinase pathways mediates oncogenic ras-induced premature senescence. *Molecular and cellular biology* 22: 3389-3403.

Yang N C, Hu M L (2005) The limitations and validities of senescence associated-betagalactosidase activity as an aging marker for human foreskin fibroblast Hs68 cells. *Experimental gerontology* 40: 813-819.

Zhang H, Cohen S N (2004) Smurf2 up-regulation activates telomere-dependent senescence. *Genes & development* 18: 3028-3040.

The invention claimed is:

1. A method of detecting and killing a senescent cell in a subject, the method comprises measuring the expression, in a sample obtained from the subject, of at least three senescent cell biomarkers selected from DEP-1, NTAL, EBP50, STX4, VAMP3, ARMCX-3, LANCL1 on the surface of a cell, wherein an increased level of expression of the at least three biomarkers relative to the level of expression detected in a reference sample indicates the presence of a senescent cell in the sample, and administering a cytotoxic agent to the subject in an amount effective to kill the senescent cell.

2. The method according to claim 1, wherein the method comprises measuring four or more senescent cell biomarkers in the sample.

3. The method according to claim 1, wherein the sample comprises blood, plasma, serum, spinal fluid, urine, sweat, saliva, tears, breast aspirate, prostate fluid, seminal fluid, vaginal fluid, stool, cervical scraping, cytes, amniotic fluid, intraocular fluid, mucous, moisture in breath, animal tissue, cell lysates, tumour tissue, hair, skin, buccal scrapings, nails, bone marrow, cartilage, prions, bone powder, ear wax, or combinations thereof.

4. The method according to claim 1, wherein the subject is an experimental animal or a human.

5. The method according to claim 1, wherein sample is an ex vivo sample or an in vitro sample.

* * * * *